US011826199B2

(12) United States Patent
Saito et al.

(10) Patent No.: US 11,826,199 B2
(45) Date of Patent: Nov. 28, 2023

(54) ULTRASOUND PROBE AND ULTRASOUND DIAGNOSTIC APPARATUS

(71) Applicant: Konica Minolta, Inc., Tokyo (JP)

(72) Inventors: Koetsu Saito, Osaka (JP); Hisashi Minemoto, Hirakata (JP)

(73) Assignee: KONICA MINOLTA, INC., Tokyo (JP)

( * ) Notice: Subject to any disclaimer, the term of this patent is extended or adjusted under 35 U.S.C. 154(b) by 121 days.

(21) Appl. No.: 16/845,861

(22) Filed: Apr. 10, 2020

(65) Prior Publication Data

US 2020/0337677 A1 Oct. 29, 2020

(30) Foreign Application Priority Data

Apr. 23, 2019 (JP) ................ 2019-081539

(51) Int. Cl.
*A61B 8/00* (2006.01)
*G01N 29/24* (2006.01)
(Continued)

(52) U.S. Cl.
CPC .............. *A61B 8/4494* (2013.01); *A61B 8/14* (2013.01); *A61B 8/4444* (2013.01);
(Continued)

(58) Field of Classification Search
CPC ....... A61B 8/4494; A61B 8/14; A61B 8/4444; A61B 8/5207; A61B 8/4483; A61B 8/486; A61B 8/488; H01L 41/083; G01N 29/221; G01N 29/2437; B06B 1/0677; A16B 8/5207
See application file for complete search history.

(56) References Cited

U.S. PATENT DOCUMENTS 9,799,818 B2 * 10/2017 Osawa ................ A61B 8/4494
2003/0013959 A1 * 1/2003 Grunwald ........... G01S 15/8981
600/437
(Continued)

FOREIGN PATENT DOCUMENTS

JP H03-151948 A 6/1991
JP 2000-131298 A 5/2000
(Continued)

OTHER PUBLICATIONS

Mckeighen, "Design guidelines for medical ultrasonic arrays", Proc. SPIE 3341, Medical Imaging 1998: Ultrasonic Transducer Engineering, (May 1, 1998) (Year: 1998).*
(Continued)

*Primary Examiner* — Pascal M Bui Pho
*Assistant Examiner* — Amy Shafqat
(74) *Attorney, Agent, or Firm* — LUCAS & MERCANTI, LLP

(57) ABSTRACT

Disclosed is an ultrasound probe including: a piezoelectric body that transmits and receives ultrasound; a backing that is disposed behind the piezoelectric body; and a reflector that is disposed between the piezoelectric body and the backing and that has an acoustic impedance greater than an acoustic impedance of the piezoelectric body; wherein, a thickness of the reflector is within the range of more than 0 to less than $0.05\lambda$, where $\lambda$ is a wavelength of the ultrasound.

18 Claims, 14 Drawing Sheets

(51) Int. Cl.
  *A61B 8/14*    (2006.01)
  *G01N 29/22*   (2006.01)
  *A61B 8/08*    (2006.01)
(52) U.S. Cl.
  CPC ....... *G01N 29/221* (2013.01); *G01N 29/2437* (2013.01); *A61B 8/5207* (2013.01)

(56) References Cited

U.S. PATENT DOCUMENTS

| | | | | |
|---|---|---|---|---|
| 2013/0310688 | A1* | 11/2013 | Rosen | A61B 8/0825 600/437 |
| 2013/0315035 | A1* | 11/2013 | Tai | B06B 1/0622 367/140 |
| 2016/0288169 | A1* | 10/2016 | Bae | H01L 41/253 |
| 2018/0040805 | A1* | 2/2018 | Motoki | A61B 8/14 |
| 2020/0253584 | A1* | 8/2020 | Morimoto | B06B 1/0681 |

FOREIGN PATENT DOCUMENTS

| | | | |
|---|---|---|---|
| JP | 2011-004395 A | | 1/2011 |
| JP | 2011-030062 A | | 2/2011 |
| JP | 2011030062 A | * | 2/2011 ............. H04R 17/00 |

OTHER PUBLICATIONS

Lee et al., "A quarter-wavelength vibration mode transducer using clamped boundary backing layer", The 2012 World Congress on Advances in Civil, Environmental, and Materials Research (ACEM' 12), Seoul, Korea, Aug. 26-30, 2012 (Year: 2012).*

Office Action/Search Report dated Nov. 22, 2022 for Japanese Application No. 2019-081539, with English translation.

* cited by examiner

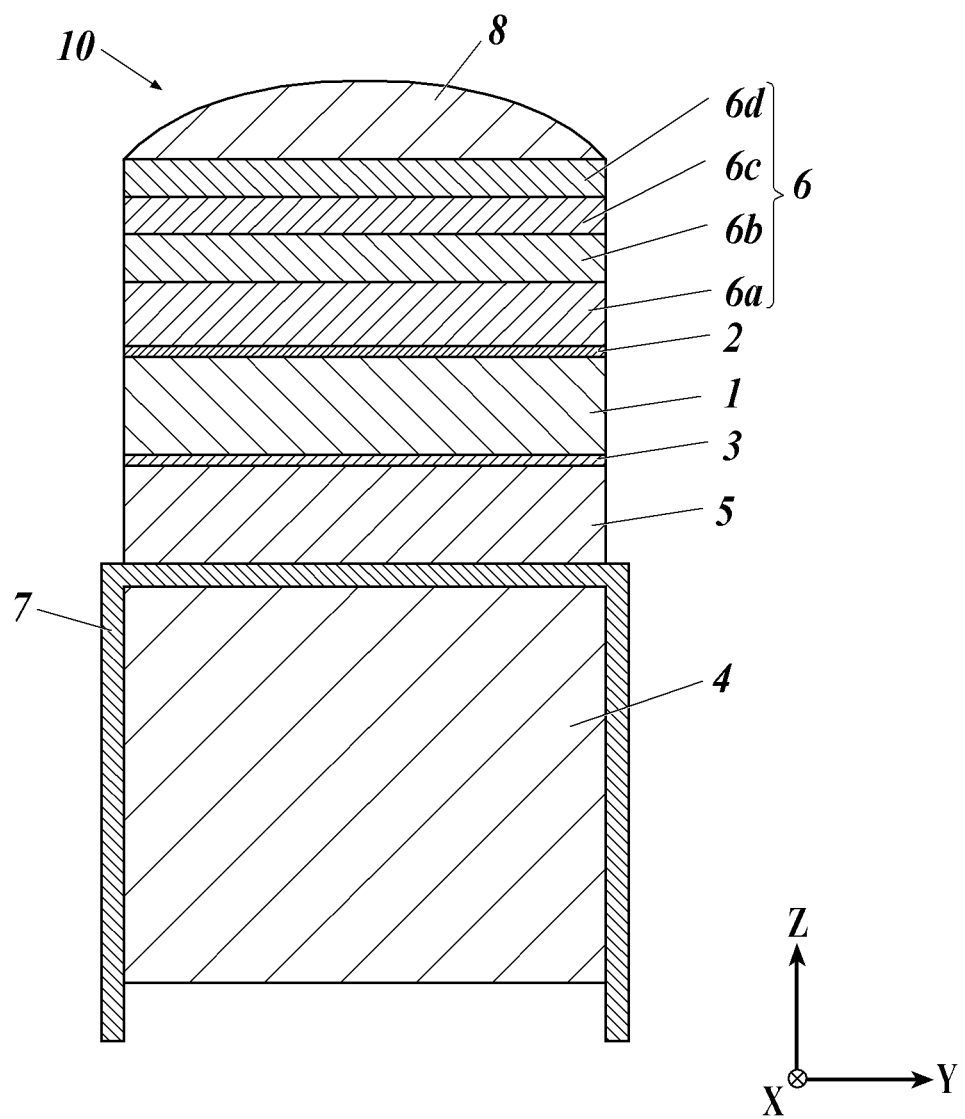

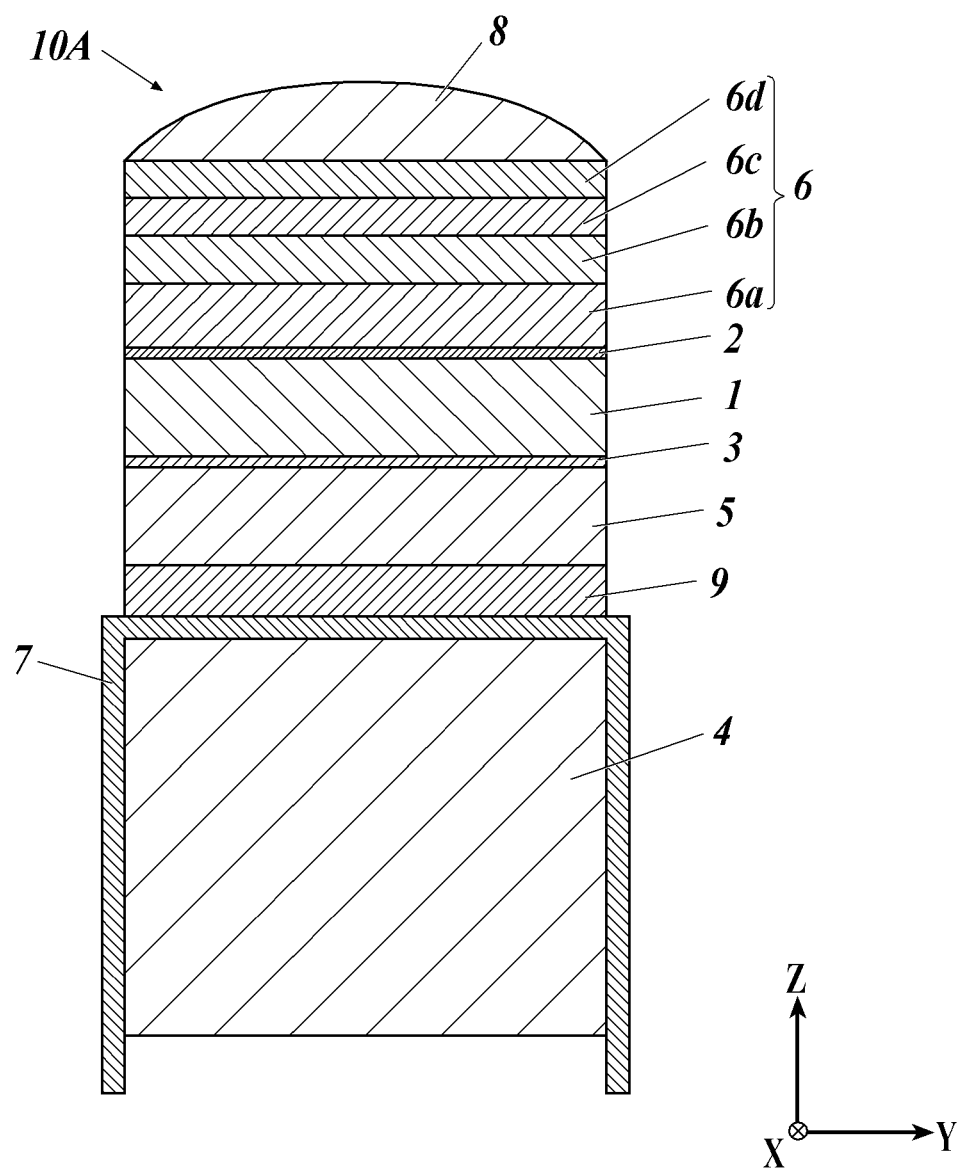

ULTRASOUND PROBE AND ULTRASOUND DIAGNOSTIC APPARATUS

CROSS-REFERENCE TO RELATED APPLICATIONS

The entire disclosure of Japanese Patent Application No. 2019-081539 filed on Apr. 23, 2019 is incorporated herein by reference in its entirety.

BACKGROUND

Field of the Invention

The present invention relates to an ultrasound probe and an ultrasound diagnostic apparatus.

Description of the Related Art

An ultrasound diagnostic apparatus is used to obtain ultrasound diagnostic images of internal forms and movements of a subject with simple actions in which an ultrasound probe connected to or communicable with the ultrasound diagnostic apparatus is put on the body surface or inserted into the body of the subject. As an advantage, an examination using the ultrasound diagnostic apparatus can be repeatedly performed because of its high safety.

The ultrasound probe incorporates a piezoelectric element(s) for transmitting ultrasound. The piezoelectric elements convert transmission signals from the ultrasound diagnostic apparatus into ultrasound signals, transmit them, receive the ultrasound reflected from the inside of the subject, convert them into electrical signals, and transmit reception signals of the converted electrical signals to the ultrasound diagnostic apparatus.

FIG. 17 is a perspective view of a conventional ultrasound probe 40. In FIG. 17, the ultrasound probe 40 includes piezoelectric elements 41, acoustic matching layers 46, backings 44, and an acoustic lens 48. The X, Y, Z axes are defined as shown in FIG. 17.

The piezoelectric elements 41 are a plurality of arranged transducers for transmission/reception of the ultrasound from/to the subject (not shown in the drawings). Each acoustic matching layer 46 is formed of one or more layers disposed in front (+Z direction) of each of the piezoelectric elements 41 on the subject side. Here, the acoustic matching layer 46 is formed of matching layers 46a, 46b, and 46c. Each backing 44 is disposed behind each of the piezoelectric elements 41, that is, on the opposite side of the matching layer 46 viewed from the piezoelectric element 41. The acoustic lens 48 is disposed on the surface of the acoustic matching layer 46 on the subject side (+Z direction).

In front of and behind the piezoelectric element 41, the electrodes not shown in the drawings are respectively disposed, and a voltage is applied to the electrodes so as to vibrate the piezoelectric element 41, and then the electrodes transmit and receive the ultrasound. The ultrasound is then transmitted and received in electrical signals.

A voltage transmitted from the main body of the ultrasound diagnostic apparatus is converted into ultrasound, and transmitted internally to the subject by the piezoelectric element 41. The reflection ultrasound (echo) reflected from the subject is converted into electrical signals and received by the piezoelectric element 41. In FIG. 17, the piezoelectric elements 41 are arranged in the X direction. Such an arrangement of the plurality of piezoelectric elements 41 is called an electronic scanning type. In this type of electronic ultrasound scanning, ultrasound beam can be deflected or converged by phase control, and the piezoelectric elements 41 are electronically switched in sequence for scanning so that the ultrasound tomography is performed in real time. Alternatively, the ultrasound tomography may be performed by mechanical scanning of a single piezoelectric element.

In FIG. 17, the reflection layer 45 is disposed between the piezoelectric element 41 and the backing 44 so that the frequency is broadened and that the sensitivity is improved. In detail, as the reflection layer 45 that has an acoustic impedance greater than that of the piezoelectric element 41 and a thickness of approximately a quarter wavelength of that of the piezoelectric element 41 is disposed behind the piezoelectric element 41, the ultrasound can be efficiently transmitted toward the subject side (for example, see JP 2000-131298 A).

However, in a case where the reflection layer 45 has an acoustic impedance not very different from that of that of the piezoelectric element 41, the reflection layer 45 is partly vibrated, and the ultrasound is reflected from the boundary of the reflection layer 45 and the backing 44, problematically. The ultrasound reflected from the boundary is transmitted toward the subject again, and such multiple reflection is shown as an artifact on the ultrasound image. Uneven patterns may be disposed on the surface of the reflection layer 45 facing away from the piezoelectric element 41 in a known technique in view of suppressing such multiple reflection (for example, see JP 2011-030062 A).

SUMMARY

There is demand for an ultrasound diagnostic apparatus that has higher resolution, and it is important to expand capacities of a ultrasound probe connected to the ultrasound diagnostic apparatus, including broadening of the frequency and improvement of the sensitivity, for higher resolution.

Improvement of the sensitivity and broadening of the frequency of the ultrasound probe are options for meeting the demand for higher resolution. A reflection layer having an acoustic impedance greater than that of the piezoelectric element may be disposed on the back surface of the piezoelectric element, as a way to achieve that. However, problematically, high reflection on the end surface of the reflection layer may cause multiple reflection that is shown as an artifact on the ultrasound image, resulting in a misdiagnosis. A structure or method for suppressing multiple reflection is not disclosed in JP 2000-131298 A.

In JP 2011-030062 A, the end surface of the reflection layer is an uneven surface, as a structure for suppressing multiple reflection. The uneven pattern has a thickness of approximately 10% of that of the reflection layer, but multiple reflection may not be suppressed sufficiently with such a structure.

An object of the present invention is to provide an ultrasound probe and an ultrasound diagnostic apparatus in which multiple reflection is suppressed for improvement of the sensitivity and broadening of the frequency of the ultrasound probe.

To achieve at least one of the abovementioned objects, an ultrasound probe reflecting one aspect of the present invention includes:

a piezoelectric body that transmits and receives ultrasound;

a backing that is disposed behind the piezoelectric body; and a reflector that is disposed between the piezoelectric body and the backing and that has an acoustic impedance greater than an acoustic impedance of the piezoelectric body;

wherein, a thickness of the reflector is within the range of more than 0 to less than $0.05\lambda$, where $\lambda$ is a wavelength of the ultrasound.

To achieve at least one of the abovementioned objects, an ultrasound diagnostic apparatus reflecting another aspect of the present invention includes:

the ultrasound probe as described above;

a transmitter that generates a driving signal and outputs the driving signal to the ultrasound probe; and an image generator that generates ultrasound image data based on a reception signal input from the ultrasound probe.

BRIEF DESCRIPTION OF THE DRAWINGS

The advantages and features provided by one or more embodiments of the invention will become more fully understood from the detailed description given hereinbelow and the appended drawings which are given by way of illustration only, and thus are no intended as a definition of the limits of the present invention, wherein:

FIG. 3 is a partial cross-sectional view of an ultrasound probe in a first embodiment;

FIG. 7 is a partial cross-sectional view of an ultrasound probe in a third embodiment;

DETAILED DESCRIPTION OF THE EMBODIMENTS

The first to fourth embodiments of the present invention are described in detail with reference to the accompanying drawings in order. However, the present invention is not limited to the illustrated examples.

First Embodiment

Figure 1:
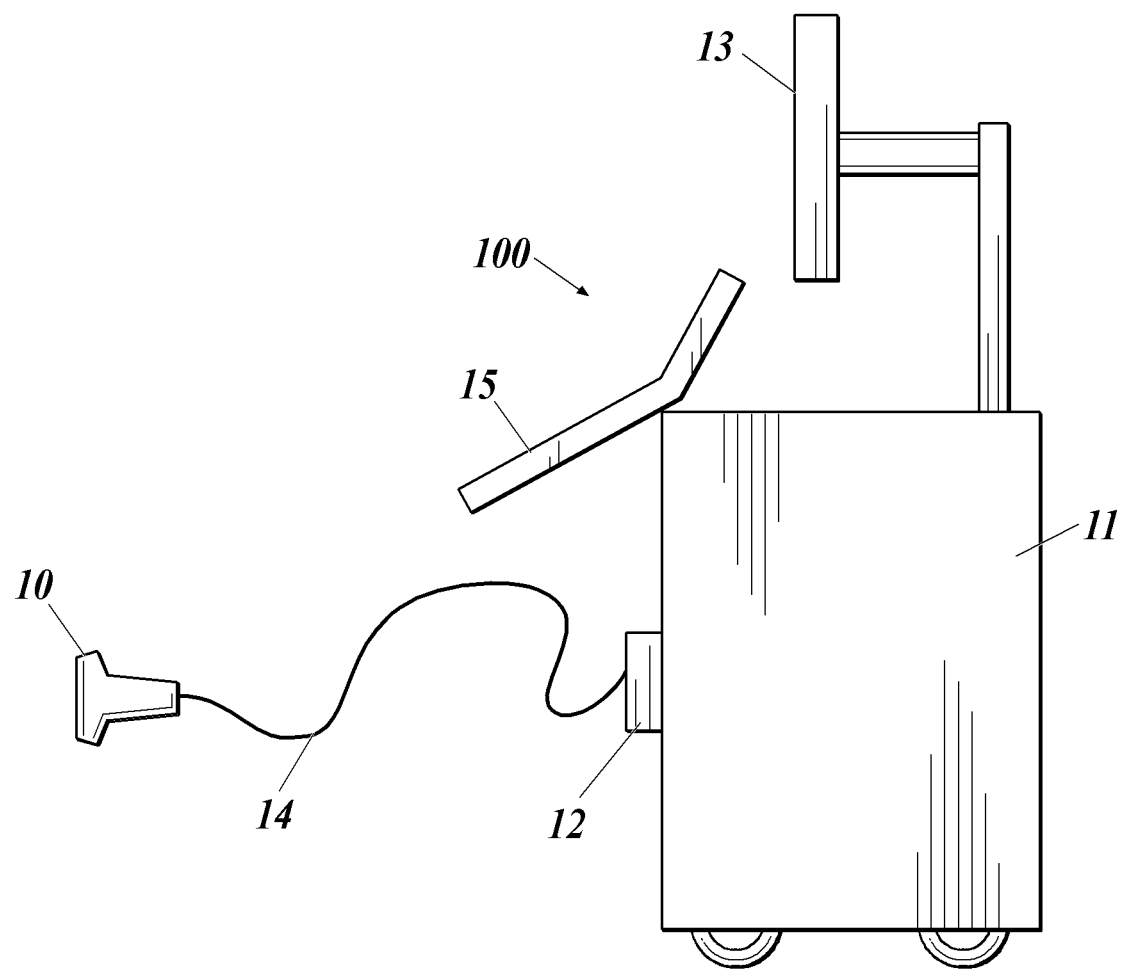
FIG. 1 is a outer view of an ultrasound diagnostic apparatus in embodiments of the present invention.

The first embodiment of the present invention is described with reference to FIGS. 1 to 5. First, the overall configuration of an ultrasound diagnostic apparatus 100 in this embodiment is described with reference to FIG. 1. FIG. 1 is a schematic drawing of the ultrasound diagnostic apparatus 100 in this embodiment.

As shown in FIG. 1, the ultrasound diagnostic apparatus 100 includes an ultrasound probe 10, a main body 11, and a connector 12. The ultrasound probe 10 is connected to the main body 11 via a cable 14. The cable 14 is connected to the connector 12. The transmission signals (driving signals) as electrical signals from the main body 11 are transmitted to a piezoelectric element(s) 1 (see FIG. 2) as a piezoelectric unit of the ultrasound probe 10 via the cable 14. The transmission signals are converted into ultrasound in the piezoelectric elements 1, and transmitted into the living body of the subject. The transmitted ultrasound is reflected from tissues or the like in the living body. Part of the reflected ultrasound is received by the piezoelectric elements 1 and converted into reception signals as electrical signals. The reception signals are transmitted to the main body 11. The reception signals are converted in the main body 11 into ultrasound image data, which is an imaged internal state of the subject, to be displayed on the display 13.

For example, the ultrasound probe 10 includes piezoelectric elements 1 as transducers. The piezoelectric elements 1 are arranged in a one-dimensional array in the lateral direction (scanning direction). In this embodiment, the ultrasound probe 10 includes 192 piezoelectric elements 1, for example. The piezoelectric elements 1 may be arranged in a two-dimensional array. The number of piezoelectric elements 1 may be suitably determined. In this embodiment, a convex electronic scanning probe is used as the ultrasound probe 10 for ultrasound scanning of the convex scanning type, but the linear scanning type or the sector scanning type may also be adopted. Communication between the main body 11 and the ultrasound probe 10 may be wireless communication such as ultra-wideband (UWB) communication, instead of wire communication through the cable 14.

Figure 2:
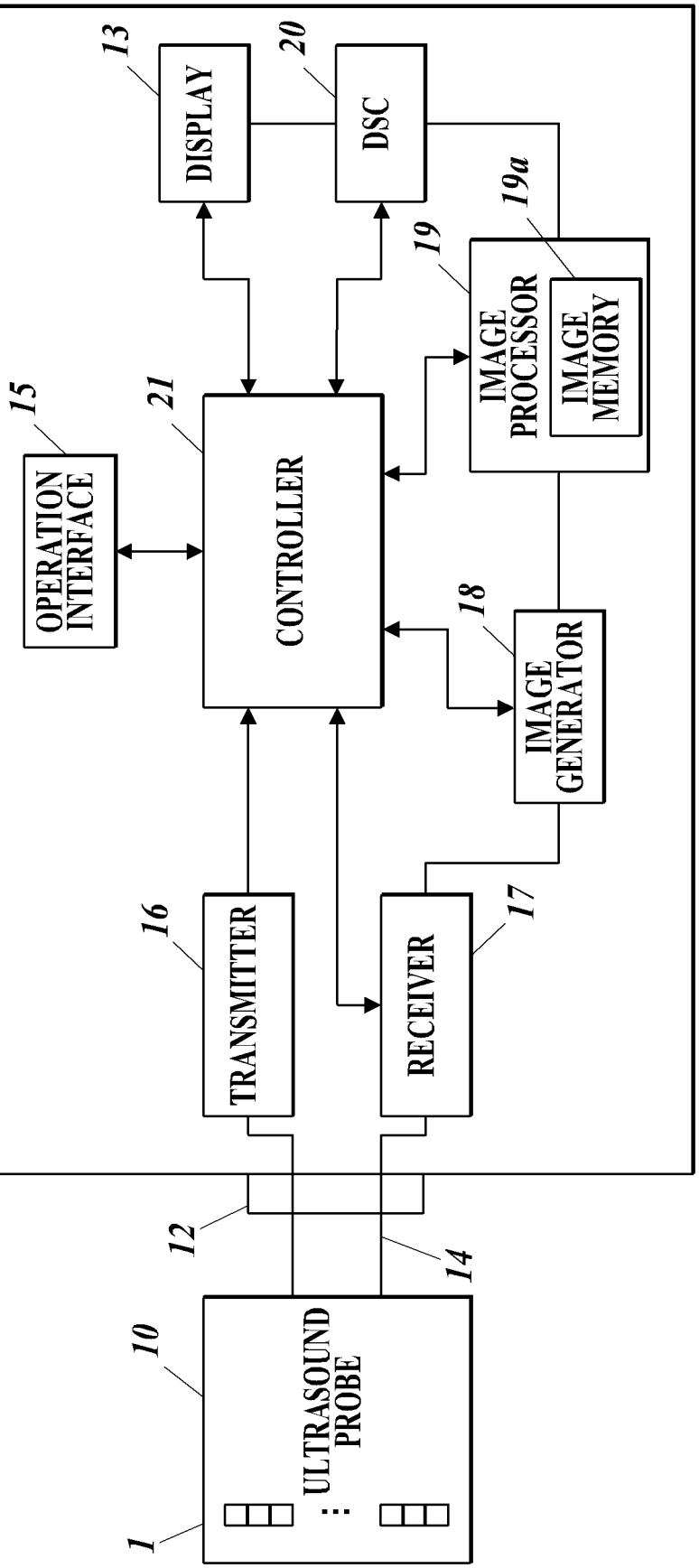
FIG. 2 is a block diagram showing a functional configuration of the ultrasound diagnostic apparatus.

Next, the functional configuration of the ultrasound diagnostic apparatus 100 is described with reference to FIG. 2. FIG. 2 is a block diagram showing the functional configuration of the ultrasound diagnostic apparatus 100.

As shown in FIG. 2, the main body 11 includes, for example, an operation interface 15, a transmitter 16, a receiver 17, an image generator 18, an image processor 19, a digital scan convertor (DSC) 20, the display 13, and a controller 21.

The operation interface 15 receives operation inputs by an operator such as a doctor and a technologist. The operation interface 15 includes, for example, various switches, buttons, a track ball, a mouse, and a keyboard for inputting an command instructing start of diagnosis, and various image parameters for displaying data such as personal information of the subject, ultrasound image data, and the like on the display 13. The operation interface 15 outputs operation signals to the controller 21. The main body 11 may include a touch panel that is overlaid on a display panel of the display 13 and that receives touch inputs by the operator.

The transmitter 16 is a circuit that supplies electrical driving signals to the ultrasound probe 10 via the cable 14 under the control of the controller 21 to cause the ultrasound probe 10 to generate transmission ultrasound. The transmitted 6 includes, for example, a clock generator circuit, a delay circuit and a pulse generator circuit. The clock generator circuit generates clock signals that determine transmission timing and transmission frequency of driving signals.

The delay circuit sets delay time for each pathway corresponding to each of the piezoelectric elements 1, and delays transmission of the driving signals by the set delay times so that transmission beams of transmission ultrasound converge. The pulse generator circuit generates pulse signals as driving signals at predetermined intervals. For example, the transmitter 16 described above generates transmission ultrasound by driving a part of the piezoelectric elements 1 (e.g. 64 adjacent elements of the 192 elements) arranged in the ultrasound probe 10. Then, the transmitter 16 shifts the active piezoelectric elements 1 in the lateral direction (scanning direction) every time transmission ultrasound is generated, so as to scan the subject.

The receiver 17 is a circuit that receives reception signals, which are electrical signals, via the cable 14 from the ultrasound probe 10 in accordance with the control by the controller 21. The receiver 17 includes, for example, an amplifier, an A/D converter circuit and a delay and sum circuit. The amplifier amplifies the reception signals at a predetermined amplification factor with respect to each of individual pathways corresponding to the respective piezoelectric elements 1. The A/D converter circuit performs analog-digital conversion (A/D conversion) on the amplified reception signals. The delay and sum circuits aligns the time phase of the A/D converted reception signals by adding a delay time with respect to each of the individual pathways corresponding to the respective piezoelectric elements 1 and sums the aligned reception signals (performs delay and sum) to generate the sound ray data.

Under the control of the system controller 21, the image generator 18 performs envelope demodulation and logarithmic compression on the sound ray data from the receiver 17 and further adjusts the dynamic range and the gain for conversion to brightness. The signal processor 33 generates a B-mode (brightness-mode) image data of pixels with a brightness value as reception energy thereby. That is, the B-mode image data represents the intensity of the reception signals by brightness. The image generator 18 may generate ultrasound image data of an imaging mode other than the B-mode, such as A-mode (Amplitude), M-mode (Motion), and color Doppler imaging mode (of the Doppler method).

The image processor 19 performs image processing on the B-mode image data output from the image generator 18 according to various kinds of image parameters under the control of the controller 21. The image processor 19 includes an image memory 19a composed of a semiconductor memory, such as a dynamic random access memory (DRAM). The image processer 19 stores the processed B-mode image data in the image memory 19a frame by frame under the control of the controller 21. The image data composed of frames may be referred to as ultrasound image data or frame image data. The image processor 19 sequentially outputs the image data thus generated to the DSC 20 under the control of the controller 21.

The DSC 20 converts the image data received from the image processor 19 into image signals for display and outputs the image signals to the display 13, under the control of the controller 21.

The display 13 may be constituted by a display device such as an LCD (Liquid Crystal Display), a CRT (Cathode-Ray Tube) display, an organic EL (Electronic Luminescence) display, an inorganic EL display or a plasma display.

Under the control of the controller 21, the display 13 displays a still image or a movie of the ultrasound image data on the display screen according to the image signals output from the DSC 20.

The controller 21 includes, for example, a central processing unit (CPU), a read only memory (ROM) and a random access memory (RAM). The controller 21 reads out various processing programs such as a system program stored in the ROM and loads them onto the RAM, and controls the components of the ultrasound diagnostic apparatus 100 in accordance with the loaded programs. The ROM, which is formed of a nonvolatile memory or the like such as a semiconductor, stores a system program for the ultrasound diagnostic apparatus 100, various processing programs executable on the system program, and various types of data such as a gamma table. These programs are stored in the form of computer readable program codes, and the CPU operates following the program codes. The RAM provides a work area where the various programs to be executed by the CPU and data relevant to the programs are temporarily stored.

Regarding the components of the ultrasound diagnostic apparatus 100, the functions of part or all of the functional blocks thereof can be achieved by a hardware circuit such as an integrated circuit. For example, the integrated circuit is an large scale integration (LSI). Depending on the degree of integration, an LSI may also be referred to as an integrated circuit (IC), a system LSI, a super LSI, or an ultra LSI.

The method for forming the integrated circuit is not limited to LSI, and hence the functions may be achieved by a dedicated circuit or a versatile processor, or achieved by making use of an FPGA (Field Programmable Gate Array) or a reconfigurable processor that can reconfigure connection and setting of circuit cells in LSI. Alternatively, all or some of the functions of the respective function blocks may be performed by software. In this case, the software is stored in one or more of storage media, such as ROMs, optical disks and hard disks, and performed by an arithmetic logic unit.

Next, an example of the overall configuration of the ultrasound probe 10 with reference to FIG. 3. FIG. 3 is a partial cross-sectional view of the ultrasound probe 10.

As shown in FIG. 3, the ultrasound probe 10 includes a piezoelectric element 1, a ground electrode 2 and a signal electrode 3 disposed respectively in front of and behind the piezoelectric element to apply voltage to the piezoelectric element 1, a reflection layer 5 as a reflection part and a signal electric terminal 7 disposed behind the signal electrode 3, an acoustic matching layer 6 and an acoustic lens 8 disposed in the written order in front of the piezoelectric element 1, and a backing (material) 4 as a backing part disposed behind the signal electric terminal 7. The signal electrode 3 and the reflection layer 5 disposed on the piezoelectric element 1 are disposed in contact with each other in this embodiment. The X, Y, and Z axes are defined as shown in FIG. 3.

The piezoelectric elements 1 are formed by a plurality of piezoelectric bodies (transducers) that are one-dimensionally arranged in the X direction in FIG. 3 and that transmit ultrasound by voltage application. The thickness of the piezoelectric element 1 may be, for example, 0.05 mm to 0.3 mm. The piezoelectric body may be a piezoelectric ceramic such as lead zirconate titanate (PZT), a piezoelectric single crystal such as a lead magnesium niobate/lead titanate (PMN-PT) solid solution and a lead zinc niobate/lead titanate (PZN-PT) solid solution, or a composite piezoelectric body of such materials and a polymer material.

The ground electrode 2 is an electrode of gold, silver, or the like disposed on the front surface of the piezoelectric element 1 by vapor deposition, sputtering, silver baking, and the like. The signal electrode 3 is an electrode of gold, silver, or the like disposed on the back surface of the piezoelectric element 1 by vapor deposition, sputtering, silver baking, and the like. The reflection layer 5 is disposed on the back surface of the signal electrode 3 disposed on the piezoelectric element 1. The reflection layer 5 is made of a material having a greater acoustic impedance than that of the piezoelectric element 1. The piezoelectric element vibrates on a wavelength of one quarter of the ultrasound transmitted and received by the piezoelectric element 1. The signal electric terminal 7 is disposed in contact with the back surface of the reflection layer 5, and connects the signal electrode 3 to an external power disposed in the main body 11 of the ultrasound diagnostic apparatus 100 via the reflection layer 5.

The acoustic matching layer 6, which is a layer to acoustically match the piezoelectric element 1 and the acoustic lens 8, is made of a material having an intermediate value of acoustic impedance between those of the piezoelectric element 1 and the acoustic lens 8. In this embodiment, the acoustic matching layer 6 is composed of four layers, the first acoustic matching layer 6a, the second acoustic matching layer 6b, the third acoustic matching layer 6c, and the fourth acoustic matching layer 6d.

In this embodiment, the first acoustic matching layer 6a is made of a material that has an acoustic impedance of 8 to 20 MRayls, such as silicon, quartz, free-machining ceramic, a graphite material filled with metal powder, and an epoxy resin filled with filler of metal or oxide. The second acoustic matching layer 6b is made of a material that has an acoustic impedance of 6 to 12 MRayls, such as graphite, and an epoxy resin filled with filler of metal or oxide. The third acoustic matching layer 6c is made of a material that has an acoustic impedance of 3 to 6 MRayls, such as an epoxy resin filled with filler of metal or oxide. The fourth acoustic matching layer 6d is made of a material that has an acoustic impedance of 1.7 to 2.3 MRayls, such as plastics, and a resin filled with silicone rubber powder.

As the acoustic matching layer 6 is multi-layered as described above, the frequency of the ultrasound probe can be broadened. Each layer of the multi-layered acoustic matching layer 6 is preferably determined such that the acoustic impedance of each layer gradually or continuously approaches the acoustic impedance of the acoustic lens 8 as the layer is located closer to the acoustic lens 8. Each layer of the multi-layered acoustic matching layer 6 may be bonded with an adhesive agent that is commonly used in the concerning technological field, such as an epoxy-based adhesive.

The material of the acoustic matching layer 6 is not limited to materials described above. Known materials such as aluminum, aluminum alloy, magnesium alloy, magnesium glass, glass, fused quartz, copper graphite, and resin can be used. A resin may be, for example, polyethylene, polypropylene, polycarbonate, ABS resin, AAS resin, AES resin, nylon, polyphenylene oxide, polyphenylene sulfide, polyphenylene ether, polyetheretherketone, polyamideimide, polyethylene terephthalate, epoxy resin, and urethane resin.

The acoustic lens 8 is made of a soft polymer that has an acoustic impedance close to that of the living body of the subject and a sound speed different from that of the living body, and focuses the ultrasound transmitted from the piezoelectric element 1 using refraction caused by a difference in the sound speed between the living body and the acoustic lens 8, which increases the resolution. In this embodiment, the acoustic lens 8 is in a cylindrical shape which extends in the Y direction in the drawings (the direction orthogonal to the arrangement direction of the piezoelectric bodies) and which is convex in the Z direction in a case where the sound speed of the acoustic lens 8 is lower than that of the living body. The ultrasound is focused in the Y direction and is radiated toward the subject side of the ultrasound probe 10 in the acoustic lens 8. A soft polymer material may be, for example, a silicone rubber.

The reflection layer 5 is disposed between the piezoelectric element 1 (and signal electrode 3) and the signal electric terminal 7, and functions in the frequency broadening and sensitivity improvement of the ultrasound probe 10. The reflection layer 5 is made of a material having an acoustic impedance greater than that of the piezoelectric element 1 described above.

The backing 4 supports the piezoelectric element 1 and the reflection layer 5 and attenuates the ultrasound transmitted from the piezoelectric element 1 toward the back surface via the reflection layer 5. The backing 4 is usually made of synthetic rubber, natural rubber, epoxy resin, thermoplastic resin, or the like filled with a material for adjusting the acoustic impedance, attenuation, and heat dissipation.

The ultrasound probe 10 may include a window (not shown in the drawings) at a position covering the side of the ultrasound probe 10 to be in contact with the subject. The window is a protection member that allows obtainment of a three-dimensional ultrasound image by mechanically rotating, swinging, or sliding an ultrasound wave transmitting/receiving unit with the single piezoelectric element 1 to transmit/receive the ultrasound, or by mechanically rotating or swinging the ultrasound wave transmitting/receiving unit with an array of the piezoelectric elements 1 allowing electronic scan. The ultrasound probe 10 may include an acoustic medium liquid (not shown in the drawings) disposed, for example, between the window and the acoustic lens 8 for acoustically matching the window and the transmitting/receiving surface of the piezoelectric element 1.

(Reflection Layer 5)

The thickness of the piezoelectric element 1 is approximately 0.25 wavelength, which is thinner than the conventional piezoelectric elements of 0.5-wavelength resonating configuration. The electric field intensity generated in the piezoelectric element 1 when a voltage is applied is inversely proportional to the thickness of the piezoelectric element 1. Thus, the electric field intensity of the piezoelectric element 1 in this embodiment is higher than the conventional piezoelectric elements, causing a large strain (deformation). The thickness of the piezoelectric element 1 in this embodiment is approximately a half of that of the conventional piezoelectric elements of 0.5-wavelength resonating type, and thus the strain of the piezoelectric element 1 is twice as large as that of the conventional piezoelectric elements.

If the piezoelectric element 1 is vibrated with no load applied on both end surface on which the ground electrode 2 and the signal electrode 3 are disposed, 0.5-wavelength resonance is highly excited in the thickness direction, and thereby the transmission/reception frequency is increased. The reflection layer 5 with an acoustic impedance greater than that of the piezoelectric element 1 so that resonance of 0.25-wavelength is excited. This makes it possible to generate a large strain while vibration of the piezoelectric element on the back surface and increase of the transmission/reception frequency are suppressed. The acoustic energy is distributed less to the reflection layer 5 side in such a state, and as a result, the ultrasound probe with high transmission efficiency can be realized. As the thickness of the piezoelectric element 1 is thinner, the ultrasound probe with larger electric capacity, high sensitivity, and a broad bandwidth can be realized.

The material of the reflection layer 5 may be, for example, tungsten or tantalum, which has a large acoustic impedance difference from the piezoelectric element 1, but tungsten carbide is preferable in terms of manufacturing. Alternatively, a mixture of tungsten and other materials can be used.

The material of the reflection layer 5 described above, which is electrically conductive, can electrically connect the signal electrode 3 and the signal electric terminal 7 of the piezoelectric element 1. However, in a case where the reflection layer 5 is electrically insulative or semiconductive, the signal electrode 3 and the signal electric terminal 7 of the piezoelectric element 1 may be electrically connected by conductor of copper or gold formed by plating, vapor deposition, or spattering around the reflection layer 5 or in a through hole provided on the reflection layer 5.

Figure 4A:
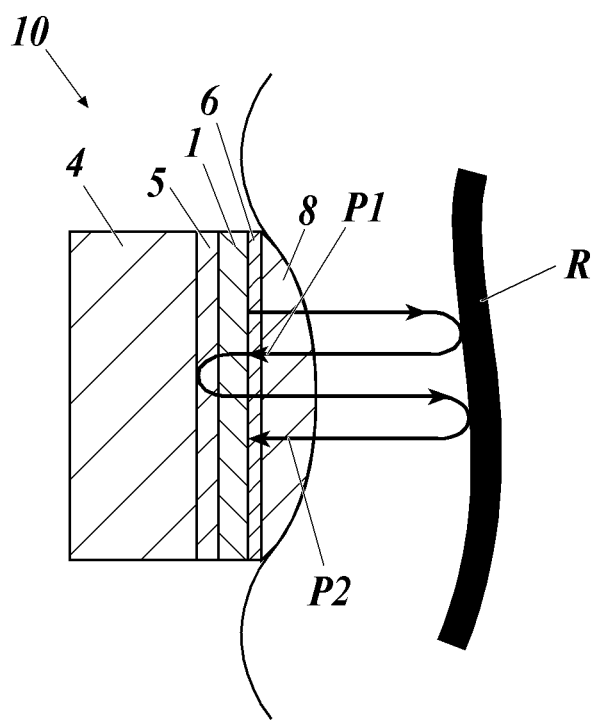
FIG. 4A is a schematic drawing of the ultrasound probe in the first embodiment in which a reflection wave and a multiple reflection wave(s) are generated.
Figure 4B:
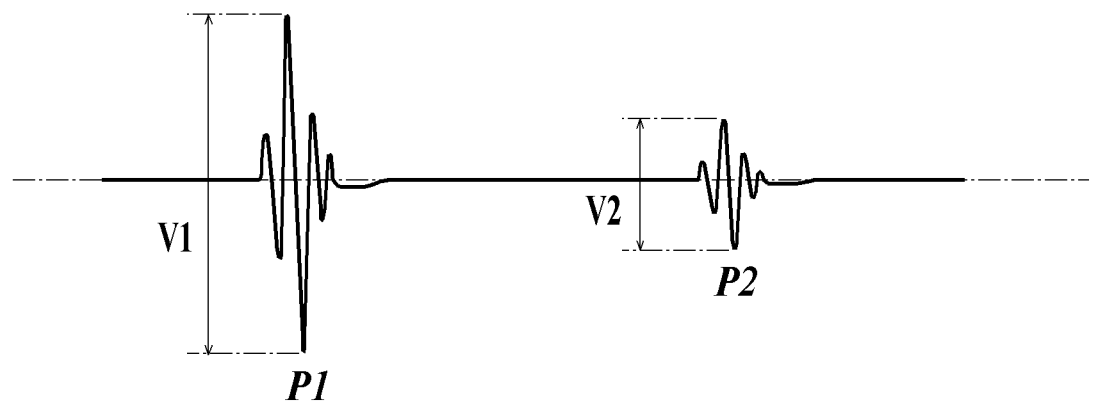
FIG. 4B shows a pulse response characteristic of the ultrasound probe in the first embodiment.

The piezoelectric element 1 with the reflection layer 5 has problems as follows beside the characteristics described above. The problems are described with reference to FIGS. 4A to 4C. FIG. 4A is a schematic drawing of the ultrasound probe 10 in which a reflection wave P1 and a multiple reflection wave P2 are generated. FIG. 4B shows a pulse response characteristic of the ultrasound probe 10.

The ultrasound probe 10 in FIG. 4A is configured similarly to that in FIG. 3. When a driving voltage is applied to the piezoelectric element 1, the piezoelectric element 1 is vibrated and the ultrasound is transmitted toward the subject (the reflection body R in FIG. 4A) via the acoustic matching layer 6 and the acoustic lens 8. The reflection wave reflected from the subject (shown as P1 in FIG. 4A) is received by the piezoelectric element 1 through the inverse path, and is converted into the electrical signals. Then, the electrical signals are transmitted to the main body of the ultrasound diagnostic apparatus and imaged in the main body. However, the received reflection wave P1 reaches the reflection layer 5, and is reflected from the boundary between the reflection layer 5 and the signal electric terminal 7 or the backing 4 because of a large acoustic impedance difference. The reflected ultrasound (multiple reflection wave shown as P2 in FIG. 4B) propagates toward the acoustic lens 8, and is transmitted toward the subject. In FIG. 4B, the horizontal axis represents time, and the vertical axis represents a voltage of response of the piezoelectric element 1.

The multiple reflection wave P2 is an unwanted wave, and such multiple reflection may be shown as an artifact on the ultrasound image and may result in a misdiagnosis. Compared with the conventional piezoelectric element with 0.5-wavelength resonating configuration, the piezoelectric element with the reflection layer 5 produces a larger multiple reflection wave P2 by 2 to 3 dB, and the difference causes the problem of multiple reflection. It is important to suppress the multiple reflection wave P2. In image diagnosis of the carotid artery in the diagnostic region of the cervix especially, multiple reflection in the carotid artery are shown as an artifact, which does not exist in reality, resulting in a misdiagnosis.

In this embodiment, the multiple reflection wave P2 is suppressed to the extent that the multiple reflection do not cause more problems than in the conventional piezoelectric element with 0.5-wavelength resonating configuration. Here, as shown in FIG. 4B, Vpp (peak to peak) of the reflection wave P1 is referred to as a voltage V1, and Vpp of the reflection wave P2 is referred to as a voltage V2.

Figure 5:
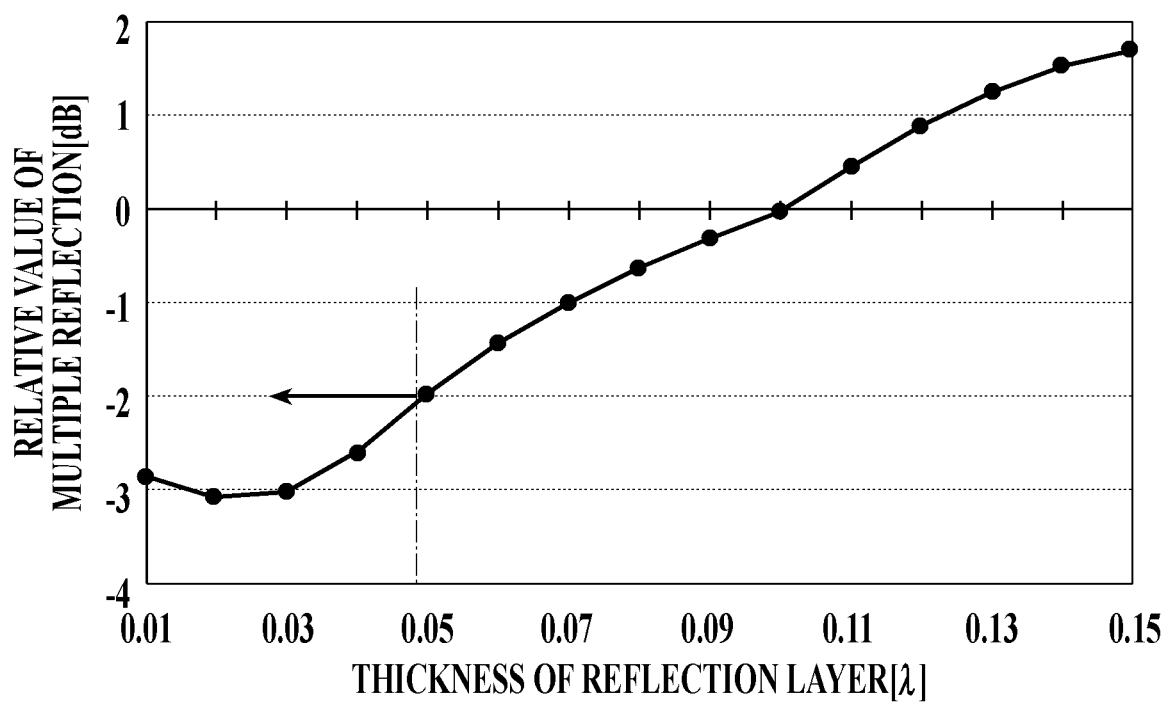
FIG. 5 is a graph showing a relationship between a thickness of a reflection layer and a relative value of multiple reflection in the ultrasound probe in the first embodiment.

FIG. 5 is a graph showing the relationship between the thickness of the reflection layer 5 and the relative value of multiple reflection in the ultrasound probe 10. The ultrasound probe 10 was tested for the reflection layer 5 with different thicknesses, which are represented by equivalents of the wavelength of the ultrasound transmission frequency. In FIG. 5, the ratio of the voltage V1 of the reflection wave P1 by primary reflection from the reflection body R and the voltage V2 of the multiple reflection wave P2 by multiple reflections as shown in FIG. 4A are represented in decibels. Further, FIG. 5 illustrates the results of relative comparison with the ratio of the voltage V1 and the voltage V2 in multiple reflections when the reflection layer 5 has a normal thickness of 0.1 time the wavelength of the ultrasound, which is set to 0 dB as a reference. Specifically, the ratio in decibels of the voltage V1 and the voltage V2 in the multiple reflections is calculated as $20 \log(V2/V1)$. The results shown in FIG. 5 were obtained by simulation of the pulse response characteristics of the ultrasound transmitted/received by the piezoelectric element 1 by the Krimholtz, Leedom and Matthaei (KLM) method, where the center frequency of the ultrasound was 10 MHz in the ultrasound probe 10 shown in FIG. 3, and the acoustic impedance of each component is as shown in Table I.

TABLE 1

| Configuration | Acoustic Impedance (MRayls) |
|---|---|
| Piezoelectric Element 1 | 30.8 |
| First Acoustic Matching Layer 6a | 13 |
| Second Acoustic Matching Layer 6b | 9.5 |
| Third Acoustic Matching Layer 6c | 4.5 |
| Fourth Acoustic Matching Layer 6d | 2 |
| Acoustic Lens 8 | 1.48 |
| Reflection Layer 5 | 94 |
| Backing 4 | 3 |

In the simulation, water was assumed to be the subject in front of the acoustic lens 8 of the ultrasound probe 10 shown in FIG. 3, and a stainless reflection plate was disposed as the reflection body R at a distance of 5 mm in the water. The voltages V1 and V2 of the reflected pulse response waveforms (the reflection wave P1 and the multiple reflection wave P2) were calculated. The thickness of the reflection layer 5 was normalized by the wavelength of the ultrasound transmitted/received by the piezoelectric elements 1.

The frequency depends on the thickness of the piezoelectric element 1 and the reflection layer 5. However, the thickness of the reflection layer 5 is preferably around 0.1 times the wavelength (approx. 0.1 wavelength), not 0.25 times the wavelength (approx. 0.25 wavelength) in regard of the frequency characteristics and the center frequency. The reference value was the relative value of multiple reflection of the reflection layer 5 of the thickness of 0.1 wavelength. As shown in FIG. 5, the simulation confirmed that multiple reflection gets stronger as the thickness of the reflection layer 5 is greater and that multiple reflection gets weaker as the thickness is less.

FIG. 5 shows that the thickness of the reflection layer 5 is to be less so as to suppress multiple reflection, with the commonly-used reflection layer 5 of a thickness of approximately 0.1 wavelength as the reference (hereinafter, the wavelength of the ultrasound transmitted/received by the piezoelectric element 1 is represented by "k").

The relative value of multiple reflection needs to be lowered by approximately more than 2 dB so that multiple reflection does not cause more problems than in the conventional piezoelectric element with 0.5λ resonating configuration. The thickness of the reflection layer 5 is to be less than 0.05λ so that the relative value of multiple reflection is raised by 2 dB or more starting from 0.1λ, the regular thickness of the reflection layer 5, as illustrated in FIG. 5. Multiple reflection can be suppressed as the thickness of the reflection layer 5 is less, but if the thickness is zero, that is, without the reflection layer 5, resonance of 0.5λ is excited in the piezoelectric element 1 as in the conventional piezoelectric element. The thickness of the reflection layer 5 is preferably less than 0.05λ excluding 0, so that resonance of 0.25λ is excited in the piezoelectric element 1.

The effectiveness of the reflection layer is gradually reduced as the thickness of the reflection layer 5 is less. The thickness of the reflection layer 5 is 0.01λ or more and less than 0.05λ, more preferably.

As described hereinbefore, in this embodiment, the ultrasound probe 10 includes the piezoelectric elements 1 that transmit/receive the ultrasound, the backings 4 that are disposed behind the piezoelectric elements 1, the reflection layers 5 that are disposed between the piezoelectric elements 1 and the backings 4 and that have an acoustic impedance greater than that of the piezoelectric elements 1. The thickness of the reflection layer 5 is less than 0.05λ excluding 0 (greater than zero), relative to the wavelength λ of the ultrasound. More preferably, the thickness of the reflection layer 5 is 0.01λ or more and less than 0.05λ relative to the wavelength λ of the ultrasound.

This can reduce multiple reflection so as not to affect the ultrasound image, facilitates improvement of the sensitivity of the ultrasound probe 10 and broadening the frequency, and improve the resolution of the ultrasound diagnostic apparatus 100.

The thickness of the reflection layer 5 is even. This makes it possible to easily manufacture the ultrasound probe 10.

The ultrasound diagnostic apparatus 100 includes the ultrasound probe 10, the transmitter 16 that generates and outputs the driving signals to the ultrasound probe 10, and the image generator 18 that generates the ultrasound image data based on the reception signals input from the ultrasound probe 10. As described above, multiple reflection can be suppressed, and improvement of the sensitivity and broadening of the frequency of the ultrasound probe 10 can be easily achieved, for higher resolution of the ultrasound diagnostic apparatus 100. Thus, the high-quality ultrasound image data without an artifact can be generated.

Second Embodiment

Figure 6A:
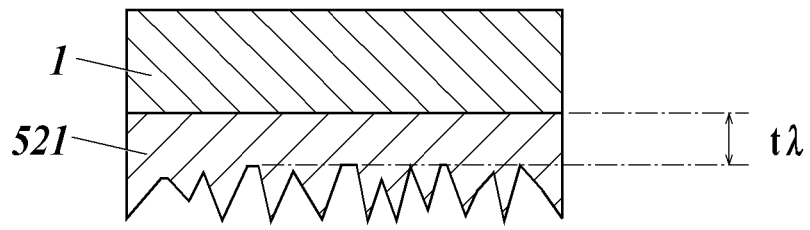
FIG. 6A shows an example of a cross-sectional view of a piezoelectric element and the reflection layer.
Figure 6B:
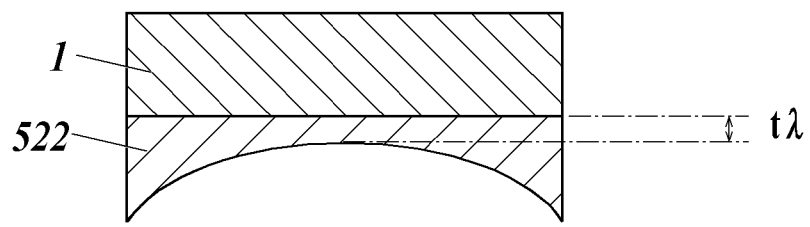
FIG. 6B shows an example of a cross-sectional view of the piezoelectric element and the reflection layer.
Figure 6C:
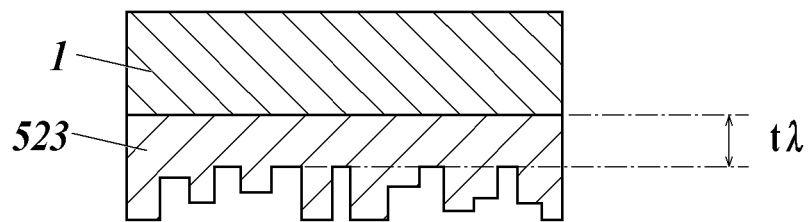
FIG. 6C shows an example of a cross-sectional view of the piezoelectric element and the reflection layer.

The second embodiment of the present invention is described with reference to FIGS. 6A to 6C. FIG. 6A is a cross-sectional view of the piezoelectric element 1 and a reflection layer 521. FIG. 6B is a cross-sectional view of the piezoelectric element 1 and a reflection layer 522. FIG. 6C is a cross-sectional view of the piezoelectric element 1 and a reflection layer 523.

In this embodiment, the configuration of the ultrasound diagnostic apparatus 100 is similar to that of the first embodiment, but the reflection layer 5 of the ultrasound probe 10 is substituted by the reflection layer 521 in FIG. 6A, the reflection layer 522 in FIG. 6B, or the reflection layer 523 in FIG. 6C. In the ultrasound diagnostic apparatus 100, the same components as those in the first embodiment are denoted by the same reference signs, and the description thereof is omitted.

Typical examples of uneven patterns on the surface of the reflection layer 5 facing away from the piezoelectric element 1 are shown in FIGS. 6A to 6C. The reflection layer 521 in FIG. 6A has a regular or irregular uneven pattern, and the thickness tλ at the thinnest point of the reflection layer 521 with the uneven pattern is within the range of more than 0 to less than 0.05 wavelength. In FIG. 6B, the reflection layer 522 is in a continuous shape that is thin at or around the central part of the piezoelectric element 1 and gets thicker toward the outer sides Similar to the reflection layer 521, the thickness tλ of the reflection layer 522 is within the range of more than 0 to less than 0.05 wavelength, at the thinnest point at or around the central part of the piezoelectric element 1, The reflection layer 523 in FIG. 6C is in a shape with regular or irregular steps (levels) in the thickness direction Similar to the reflection layer 521 in FIG. 6A, the thickness tλ of the reflection layer 523 is within the range of more than 0 to less than 0.05λ at the thinnest point.

The uneven pattern on the surface of the reflection layer 5 facing away from the piezoelectric element 41 is not necessarily one dimensional, and may be two dimensional.

Such uneven patterns may be formed on the reflection layer by machining, chemical etching, laser processing, or sandblasting.

As described above, with the uneven pattern on the end surface, the reflection layers 521, 522, and 523 scatter the reflection waves of the ultrasound. Furthermore, with the thickness a that is within the range of more than 0 to less than 0.05 wavelength at the thinnest point, the reflection layers 521, 522, and 523 can reduce multiple reflections as well as facilitate sensitivity improvement and wavelength broadening of the ultrasound. Therefore, higher resolution of the ultrasound diagnostic apparatus 100 can be achieved.

As described hereinbefore, the reflection layers 521, 522, and 523 are each uneven in thickness. This can reduce multiple reflection that affects the ultrasound image, and facilitate improvement of the sensitivity of the ultrasound probe 10 and broadening of the wavelength of the ultrasound for achieving higher resolution of the ultrasound diagnostic apparatus 100.

The unevenness in thickness of each of the reflection layers 521, 522, and 523 is continuous, gradual, regular, or irregular. Thus, the reflection layers 521, 522, 523 can be manufactured in various ways.

The reflection layers 521, 522, 523 have such uneven patterns on the opposite side from the piezoelectric element 1. This can further reduce multiple reflection that affects the ultrasound image, and further facilitate improvement of the sensitivity of the ultrasound probe 10 and broadening of the wavelength of the ultrasound for achieving even higher resolution of the ultrasound diagnostic apparatus 100.

Third Embodiment

The third embodiment of the present invention is described with reference to FIGS. 7 to 9C.

In this embodiment, the configuration of the ultrasound diagnostic apparatus 100 is similar to that of the first embodiment, but the ultrasound probe 10 is substituted by the ultrasound probe 10A in FIG. 7. In the ultrasound diagnostic apparatus 100, the same components as those in the first and second embodiments are denoted by the same reference signs, and the description thereof is omitted.

First, an example of the overall configuration of the ultrasound probe 10A with reference to FIG. 7. FIG. 7 is a partial cross-sectional view of the ultrasound probe 10A.

The ultrasound probe 10A includes an intermediate layer 9 as an intermediate part that is disposed between the reflection layer 5 and the signal electric terminal 7.

The relative values of multiple reflection are calculated for the ultrasound probe 10A with the intermediate layer 9 under the same conditions as the first embodiment. The thickness td of the reflections layer 5 (the thickness relative to the wavelength of the ultrasound transmitted/received by the piezoelectric element 1), the acoustic impedance Zm (MRayls) of the intermediate layer 9, and the thickness tm of the intermediate layer 9 (the thickness relative to the wavelength of the ultrasound transmitted/received by the piezoelectric element 1) are changed in calculation.

Figure 8:
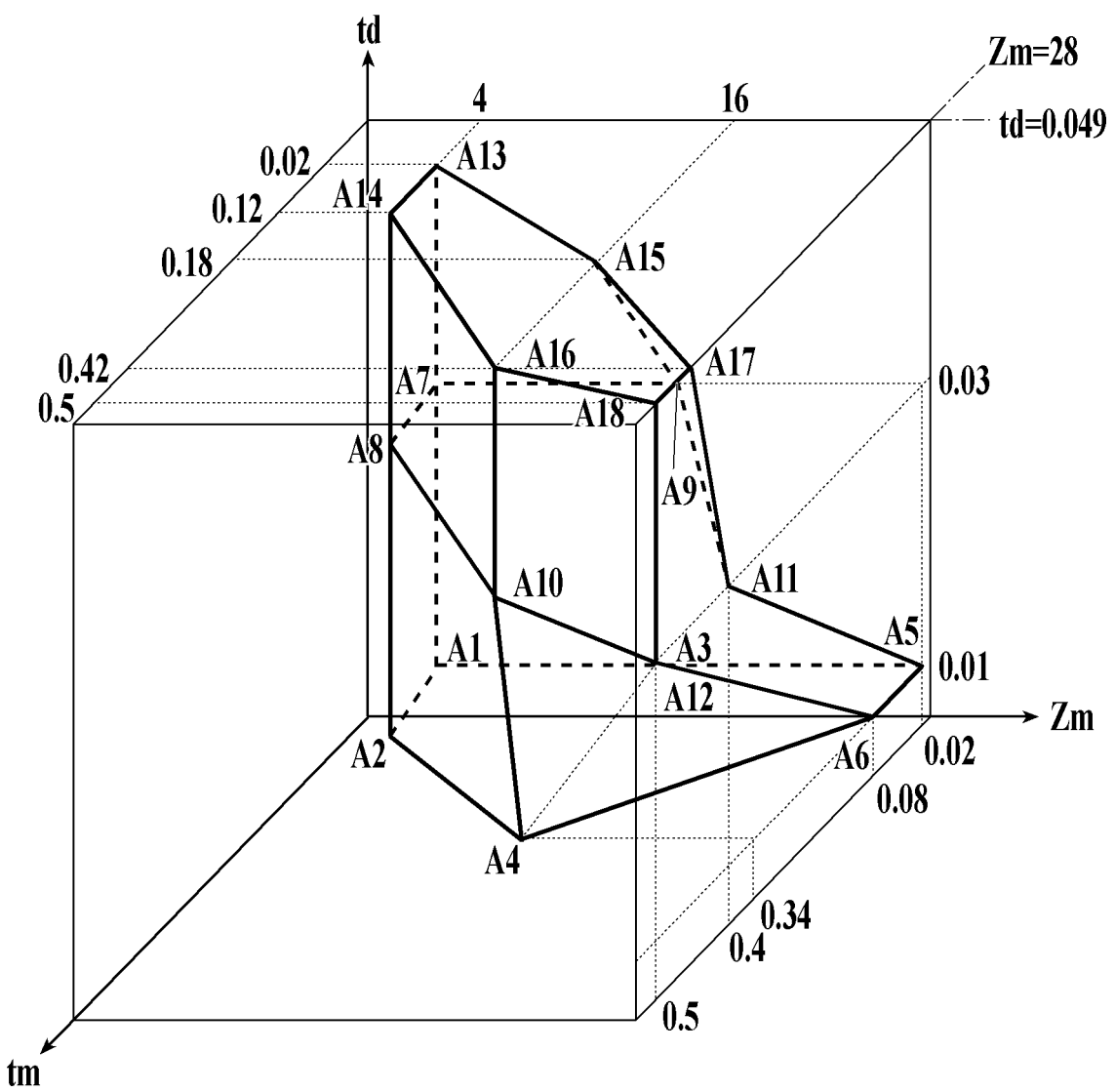
FIG. 8 schematically shows a range of a thickness of a reflection layer, an acoustic impedance of an intermediate layer, and a thickness of an intermediate layer in the ultrasound probe in the third embodiment.

FIG. 8 schematically shows the ranges of the thickness of the reflection layer 5, the acoustic impedance of the intermediate layer 9, and the thickness of the intermediate layer 9 in the ultrasound probe 10A. As a result, as shown in FIG. 8, in the orthogonal coordinates (td, Zm, tm) where the thickness td of the reflection layer 5, the acoustic impedance Zm of the intermediate layer 9, the thickness tm of the intermediate layer 9 are variables, multiple reflection can be further reduced in the area surrounded by the polyhedron with vertexes respectively at Points A1 to A18 below, that is, in the area under the conditions below.

Point A1 (0.01, 4, 0.02)
Point A2 (0.01, 4, 0.12)
Point A3 (0.01, 16, 0.02)
Point A4 (0.01, 16, 0.34)
Point A5 (0.01, 28, 0.02)
Point A6 (0.01, 28, 0.08)
Point A7 (0.03, 4, 0.02)
Point A8 (0.03, 4, 0.12)
Point A9 (0.03, 16, 0.02)
Point A10 (0.03, 16, 0.42)
Point A11 (0.03, 28, 0.4)
Point A12 (0.03, 28, 0.5)
Point A13 (0.049, 4, 0.02)
Point A14 (0.049, 4, 0.12)
Point A15 (0.049, 16, 0.18)
Point A16 (0.049, 16, 0.42)
Point A17 (0.049, 28, 0.42)
Point A18 (0.049, 28, 0.5)

In the area shown above, the relative value of the multiple reflections can be lowered by approximately 2 dB or more to the extent that multiple reflection does not cause more problems than in the conventional piezoelectric element with 0.5λ resonating configuration. In the outside area, multiple reflection tends to be greater, which is not favorable. The values defining the boundary of the area may vary, naturally, and the acceptable range of variance is approximately ±10%.

The acoustic impedance of the intermediate layer 9 is within the range of 4 to 28 MRayls, inferred from FIG. 8. Thus, the value of the acoustic impedance of the intermediate layer 9 with which the relative value of multiple reflection is lowered to an acceptable level need to be different from or less than the acoustic impedance of the backing 4, which is 3 MRayls as shown in Table 1, and also need to be different from the acoustic impedance of the reflection layer 5, which is 94 MRayls. Better results are obtained when it is below the acoustic impedance of the reflection layer 5.

The material of the intermediate layer 9 may be graphite as a conductor, a graphite material filled with metal such as copper and tungsten or a carbide, or a composite resin material filled with metal powder or an oxide.

In this embodiment, the intermediate layer 9 is a single layer, but the similar advantageous effects can be achieved with a plurality of intermediate layers 9. For example, in a case where there are two intermediate layers, multiple reflection can be further reduced when the acoustic impedance of an intermediate layer nearer to the reflection layer 5 is less than the acoustic impedance of the other intermediate layer nearer to the backing 4, or the signal electric terminal 7.

The intermediate layer 9 is preferably electrically conductive for electrical connection between the signal electrode 3 and the signal electric terminal 7 of the piezoelectric element 1. However, in a case where the intermediate layer 9 is electrically insulative or semiconductive, the signal electrode 3, the reflection layer 5, and the signal electric terminal 7 of the piezoelectric element 1 may be connected to each other by forming a conductor of copper or gold around the intermediate layer 9 or in through holes of the intermediate layer 9 by plating, vapor deposition, or spattering.

Figure 9A:
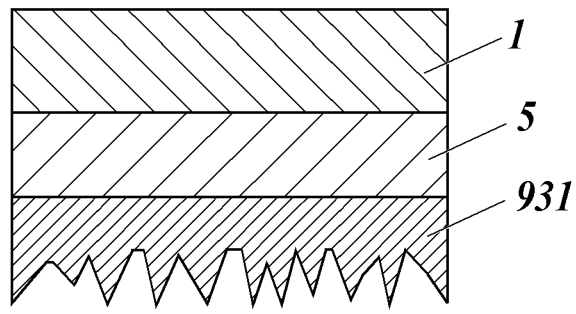
FIG. 9A is a cross-sectional view of an example of the piezoelectric element, the reflection layer, and an intermediate layer.
Figure 9B:
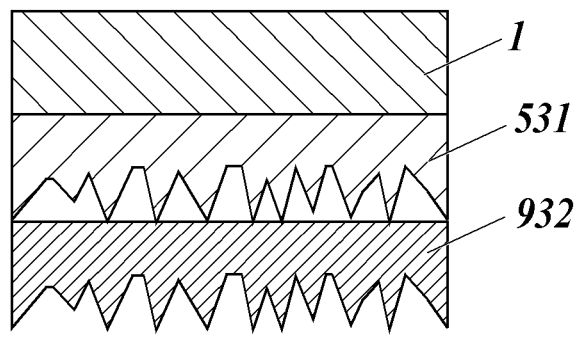
FIG. 9B is a cross-sectional view of an example of the piezoelectric element, the reflection layer, and the intermediate layer.
Figure 9C:
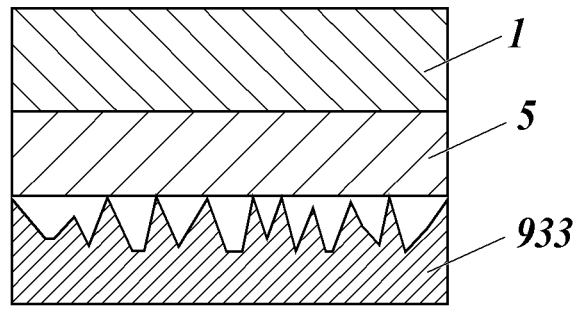
FIG. 9C is a cross-sectional view of an example of the piezoelectric element, the reflection layer, and the intermediate layer.

The intermediate layer 9 is substantially even in thickness in the above embodiment, but alternatively, the intermediate layer 9 may be configured as shown in FIGS. 9A to 9C. FIG. 9A is a cross-sectional view of the piezoelectric element 1, the reflection layer 5, and an intermediate layer 931. FIG. 9B is a cross-sectional view of the piezoelectric element 1, the reflection layer 531, and an intermediate layer 932. FIG. 9C is a cross-sectional view of the piezoelectric element 1, the reflection layer 5, and the intermediate layer 932.

As shown in FIGS. 9A to 9C, the thickness of the intermediate layer 9 is uneven, but the similar effects can be achieved regardless of whether the thickness of the intermediate layer 9 continuously or gradually varies, or whether one or both surfaces of the intermediate layer 9 are uneven in thickness. The uneven thickness of the intermediate layer 9 is preferably in the range shown in FIG. 8 at the thinnest point.

The ultrasound probe 10A in FIG. 9A includes the piezoelectric element 1, the reflection layer 5, and the intermediate layer 931. The thickness of the reflection layer 5 is substantially even and within the range of more than 0 to less than 0.05λ. The surface of the intermediate layer 931 facing the end surface of the reflection layer 5 is flat, and the opposite surface is uneven in thickness with a regular or irregular uneven pattern. In this configuration, the ultrasound transmitted from the reflection layer 5 to the intermediate layer 931 is scattered by the uneven pattern, and multiple reflection can be reduced even further. The gaps in the uneven pattern may be filled with an adhesive such as an epoxy resin.

The ultrasound probe 10A in FIG. 9B includes the piezoelectric element 1, the reflection layer 531, and the intermediate layer 932. The surface of the reflection layer 531 facing away from the end surface of the piezoelectric element 1 is uneven in thickness with a regular or irregular uneven pattern. The surface of the intermediate layer 932 facing the uneven face of the reflection layer 531 is flat, and the opposite surface of the intermediate layer 932 is uneven in thickness with a regular or irregular uneven pattern. In this configuration, the ultrasound is scattered on the uneven end surface of the reflection layer 531, and the unscattered residual ultrasound is transmitted to the intermediate layer 932 and scattered by the uneven pattern of the intermediate layer 932. Thus, multiple reflection can be further reduced. The gaps in the uneven pattern may be filled with an adhesive such as an epoxy resin. The acoustic impedance of the material disposed in the gaps is preferably less than the acoustic impedance of the intermediate layer 932 so as to be acoustically mismatched.

The ultrasound probe 10A in FIG. 9C includes the piezoelectric element 1, the reflection layer 5, and the intermediate layer 933. The reflection layer 5 is substantially even in thickness, and the surface facing the ends surface of the intermediate layer 933 is uneven in thickness with a regular or irregular uneven. In this configuration, the ultrasound can be scattered between the reflection layer 5 and the intermediate layer 933, and multiple reflection can be further reduced. The gaps in the uneven pattern may be filled with an adhesive such as an epoxy resin. The acoustic impedance of the material disposed in the gaps is preferably less than the acoustic impedance of the acoustic impedance of the intermediate layer 933 so as to be acoustically mismatched.

In this embodiment, the intermediate layer 9, 931, 932, or 933 is in contact with the reflection layer 5 or 531, as shown in FIGS. 8 to 9C. The similar advantageous effects can be achieved even when the intermediate layers 9, 931, 932, or 933 is disposed between the signal electric terminal 7 and the backing 4 and/or between the reflection layer 5 or 531 and the signal electric terminal 7.

As shown in FIGS. 9A to 9C, as a regular or irregular uneven pattern is formed on one or both surfaces of the intermediate layer 9 so that the thickness is uneven, multiple reflection can be further reduced. As a result, the sensitivity improvement and frequency broadening of the ultrasound can be achieved more easily, and the resolution of the ultrasound diagnostic apparatus 100 can be increased. As shown in FIGS. 6A to 6C, a continuous or gradual uneven pattern may be formed so that the intermediate layer 9 has an uneven thickness.

The uneven pattern on one or both surfaces of the intermediate layer 9 is not necessarily one dimensional, and may be two dimensional.

As described hereinbefore, in this embodiment, the ultrasound probe 10A includes the intermediate layer 9 that is disposed between the reflection layer 5 and the backing 4, and that has the acoustic impedance different from those of the reflection layer 5 and the backing 4. This can reduce multiple reflection so as not to affect the ultrasound image, facilitates improvement of the sensitivity of the ultrasound probe 10 and broadening the frequency, and improve the resolution of the ultrasound diagnostic apparatus 100.

The acoustic impedance of the intermediate layer 9 is greater than the acoustic impedance of the backing 4. This can reliably reduce multiple reflection so as not to affect the ultrasound image, facilitates improvement of the sensitivity of the ultrasound probe 10 and broadening the frequency more reliably, and reliably improve the resolution of the ultrasound diagnostic apparatus 100.

The thickness td of the reflection layer 5 relative to the wavelength of the ultrasound, the acoustic impedance Zm of the intermediate layer 9, and the thickness tm of the intermediate layer 9 relative to the wavelength of the ultrasound are in the area surrounded by the polyhedron with vertexes respectively at Points A1 to A18 described above in the orthogonal coordinates (rd, Zm, tm) where td, Zm, and tm are variables. This can reduce multiple reflection that affects the ultrasound image, and facilitate improvement of the sensitivity of the ultrasound probe 10 and broadening of the wavelength of the ultrasound for achieving higher resolution of the ultrasound diagnostic apparatus 100.

The material of the intermediate layer 9 is a conductor. Alternatively, the intermediate layer 9 includes an insulator material or a semiconductor material, and a conductor disposed around or penetrating the insulator material or the semiconductor material. Thus, the signal electrode 3 and the signal electric terminal 7 of the piezoelectric element 1 can be surely connected electrically to each other.

The intermediate layer 931, 932, and 933 are each uneven in thickness. This can further reduce multiple reflection so as not to affect the ultrasound image, facilitates improvement of the sensitivity of the ultrasound probe 10 and broadening the frequency more readily, and further improve the resolution of the ultrasound diagnostic apparatus 100.

The unevenness in thickness of each of the intermediate layers 931, 932 and 933 is continuous, gradual, regular, or irregular. Thus, the intermediate layers 931, 932, and 933 can be manufactured in various ways.

The intermediate layer 931 and 932 have the uneven patterns on the surface facing away from the piezoelectric element 1. This can further reduce multiple reflection that affects the ultrasound image, and further facilitate improvement of the sensitivity of the ultrasound probe 10 and broadening of the wavelength of the ultrasound for achieving even higher resolution of the ultrasound diagnostic apparatus 100.

Fourth Embodiment

The fourth embodiment of the present invention is described with reference to FIGS. 10 to 16.

Figure 10:
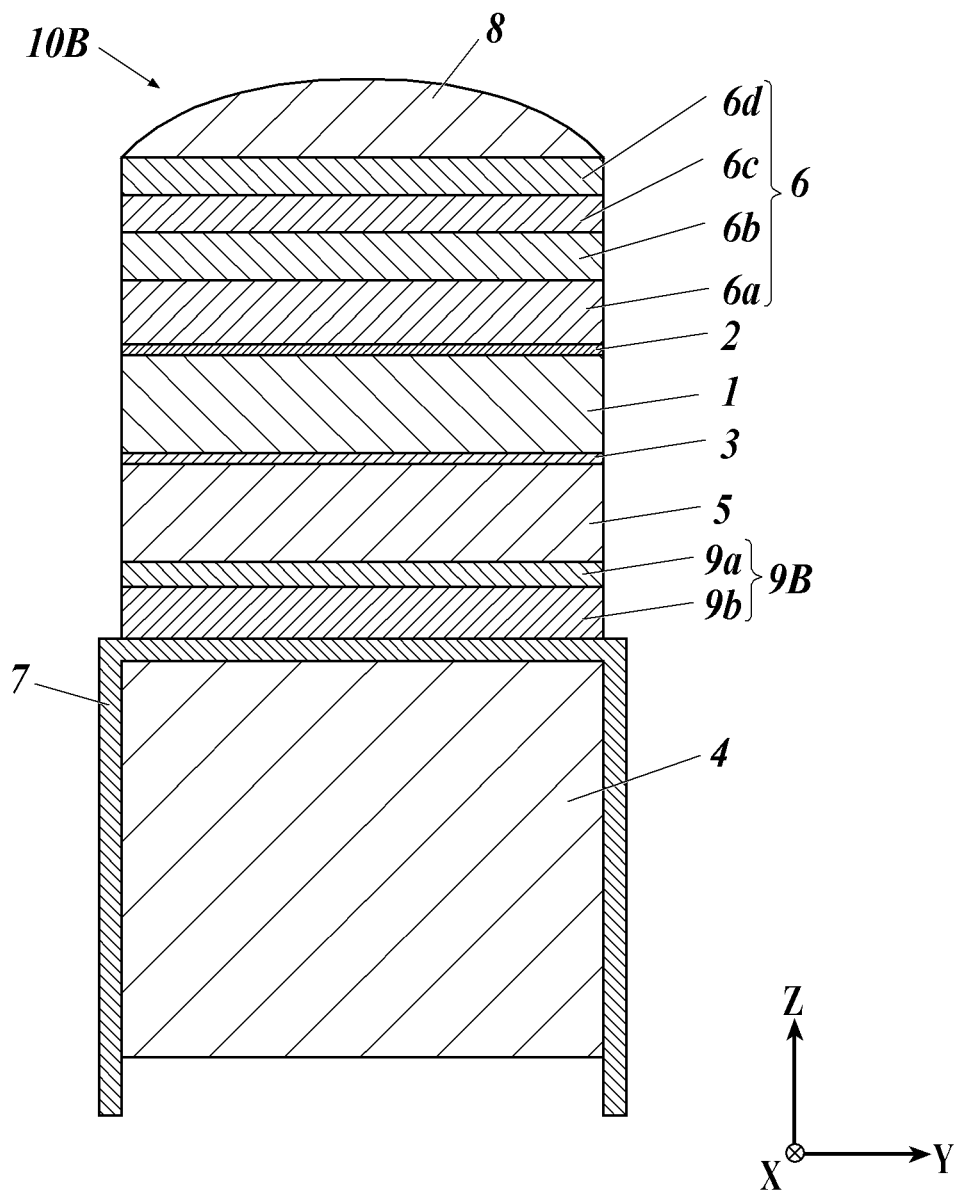
FIG. 10 is a partial cross-sectional view of an ultrasound probe in a fourth embodiment.

In this embodiment, the configuration of the ultrasound diagnostic apparatus 100 is similar to that of the first embodiment, but the ultrasound probe 10 is substituted by the ultrasound probe 10B in FIG. 10. In the ultrasound diagnostic apparatus 100, the same components as those in the first to third embodiments are denoted by the same reference signs, and the description thereof is omitted.

First, an example of the overall configuration of the ultrasound probe 10B is described with reference to FIG. 10. FIG. 10 is a partial cross-sectional view of the ultrasound probe 10B.

The ultrasound probe 10B includes an intermediate layer 9B composed of two intermediate layers 9a and 9b between the reflection layer 5 and the signal electric terminal 7. Different from the first to third embodiments, this embodiment can reduce multiple reflection with the reflective layer 5 of a thickness of 0.05λ to 0.1λ as well as the reflective layer 5 of a thickness of more than 0 to 0.05λ.

Figure 11:
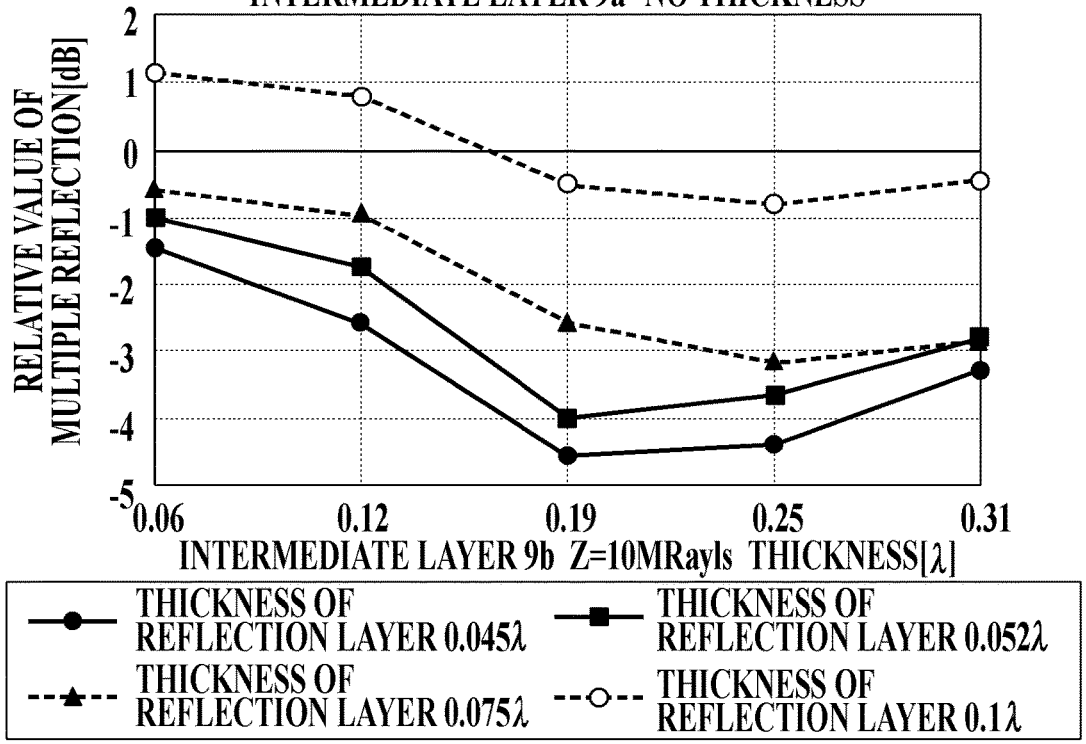
FIG. 11 is a graph when the first intermediate layer of the ultrasound probe of the fourth embodiment has no thickness, showing the relationship between the thickness of the second intermediate layer, the thickness of the reflective layer, and the relative comparison value of multiple reflections.
Figure 12:
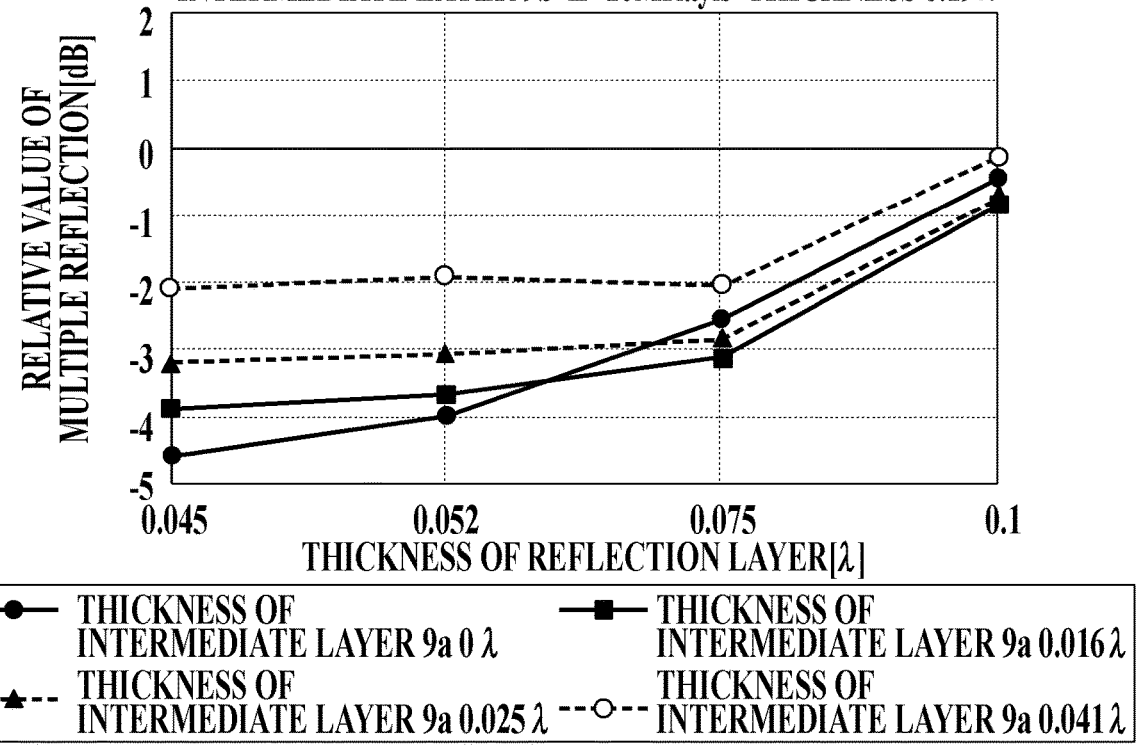
FIG. 12 is a graph when the second intermediate layer of the ultrasound probe of the fourth embodiment has a predetermined configuration, showing the relationship between the thickness of the reflection layer, the thickness of the first intermediate layer, and the relative comparison value of multiple reflections.
Figure 13:
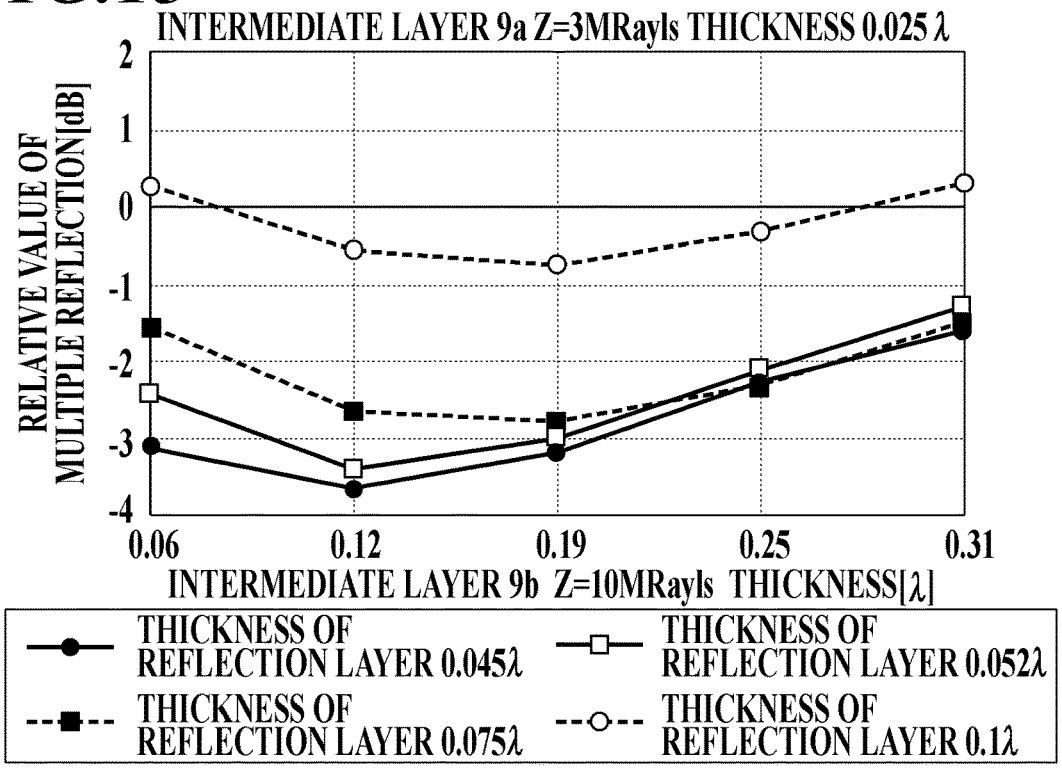
FIG. 13 is a graph when the first intermediate layer of the ultrasound probe of the fourth embodiment has a predetermined configuration, showing the relationship between the thickness of the reflection layer, the thickness of the second intermediate layer, and the relative comparison value of multiple reflections.
Figure 14:
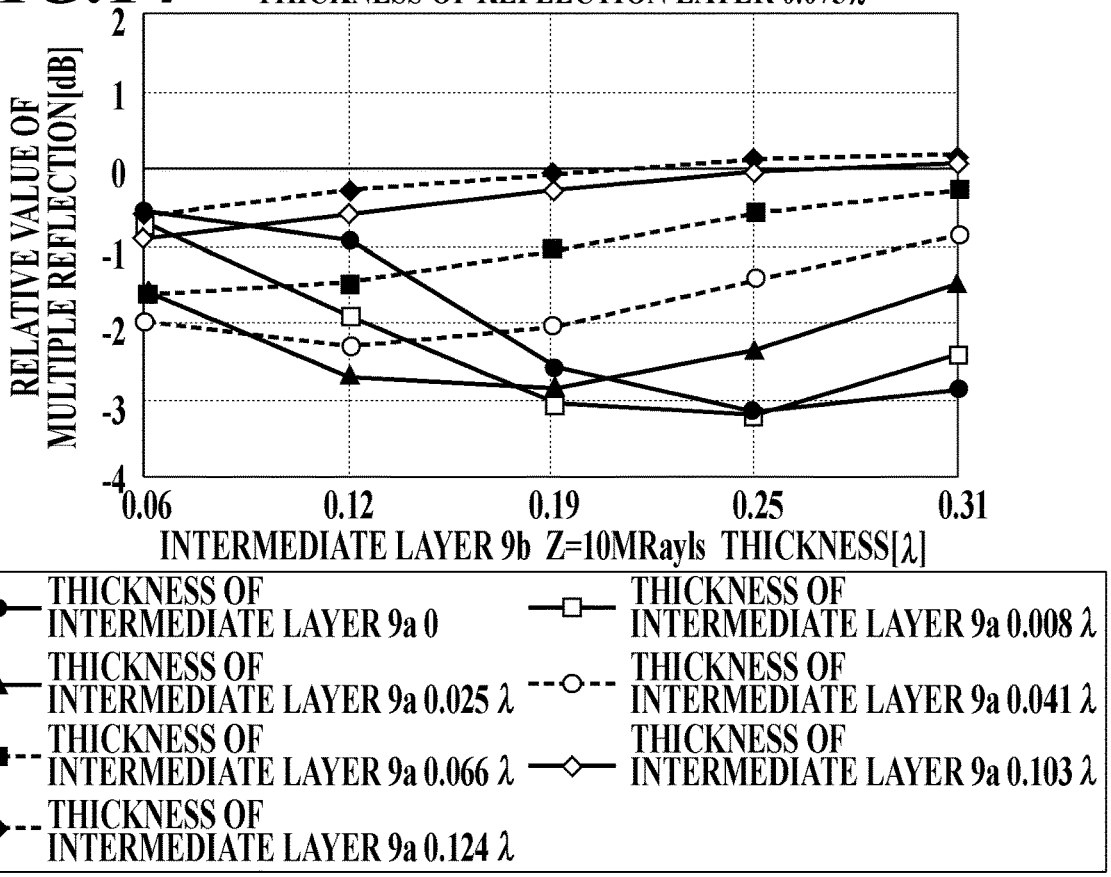
FIG. 14 is a graph when the reflection layer of the ultrasound probe of the fourth embodiment has a predetermined configuration, showing the relationship between the thickness of the second intermediate layer, the thickness of the first intermediate layer, and the relative comparison value of multiple reflections.
Figure 15:
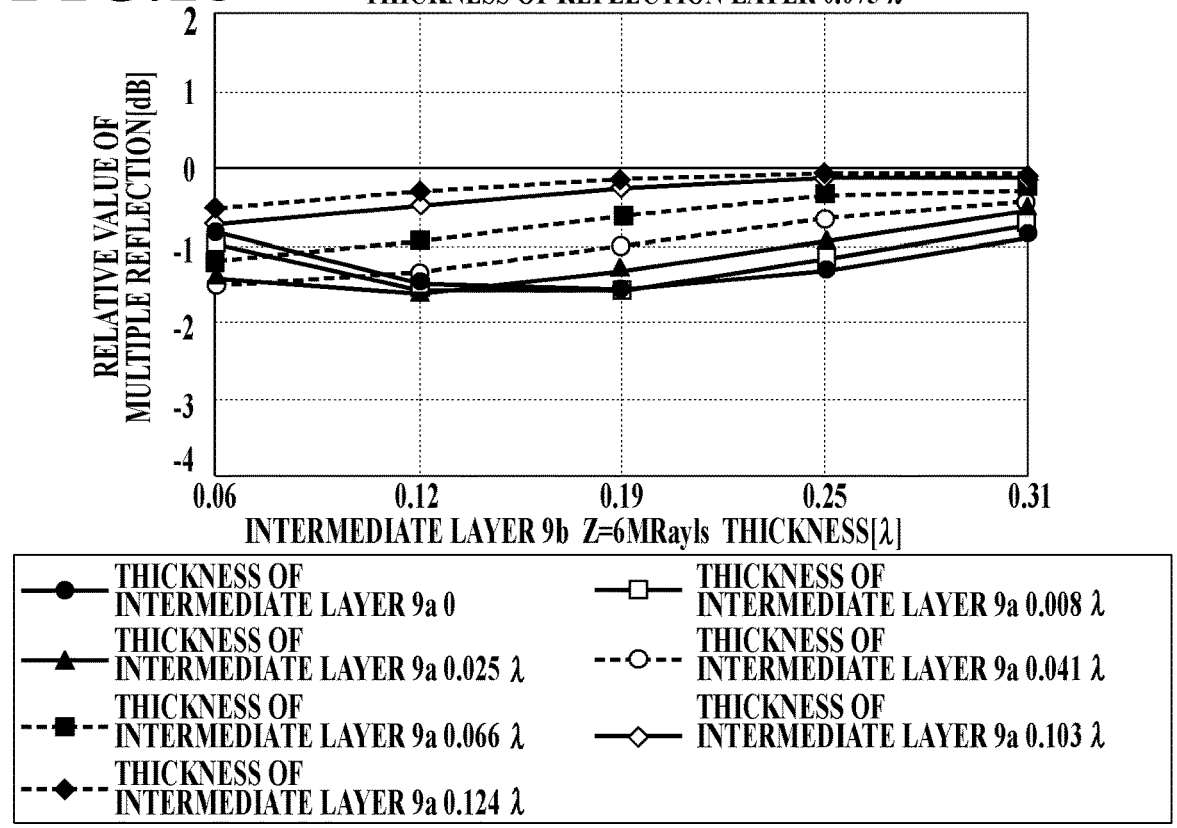
FIG. 15 is a graph when the reflection layer of the ultrasound probe of the fourth embodiment has a predetermined configuration, showing the relationship between the thickness of the second intermediate layer, the thickness of the first intermediate layer, and the relative comparison value of multiple reflections.
Figure 16:
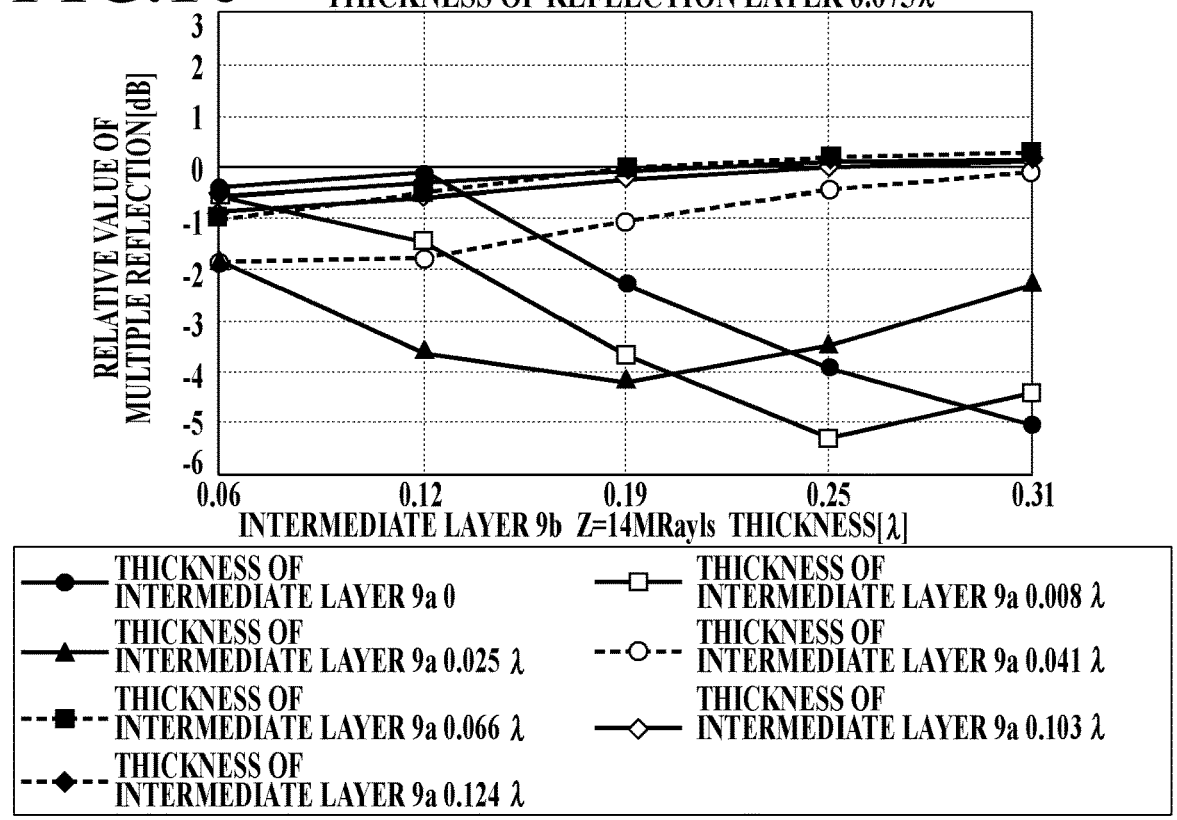
FIG. 16 is a graph when the reflection layer of the ultrasound probe of the fourth embodiment has a predetermined configuration, showing the relationship between the thickness of the second intermediate layer, the thickness of the first intermediate layer, and the relative comparison value of multiple reflections.
Figure 17:
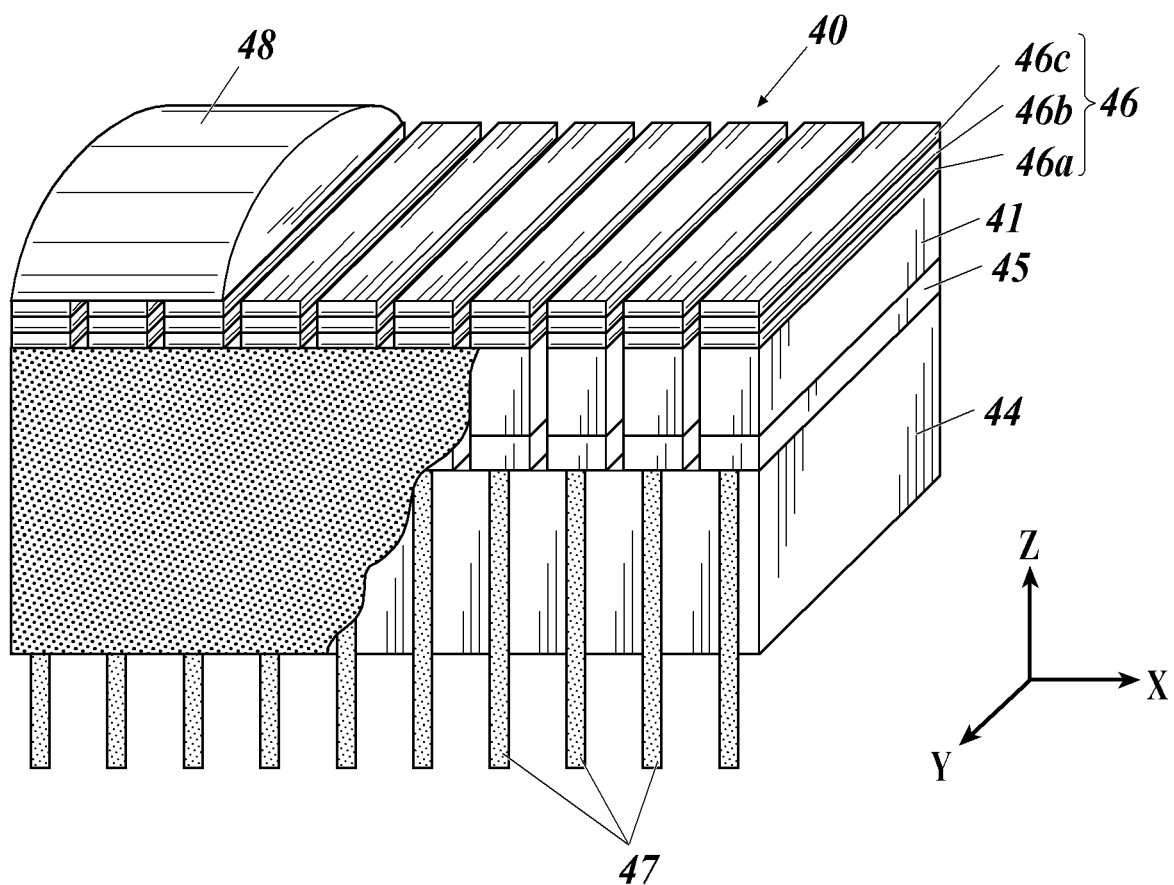
FIG. 17 is a perspective view of a conventional ultrasound probe.

Next, the relative value of multiple reflection of the ultrasound probe 10B is described with reference to FIGS. 11 to 16. FIG. 11 is a graph when the intermediate layer 9a of the ultrasound probe 10B has no thickness, showing the relations between the thickness of the intermediate layer 9b, the thickness of the reflection layer 5, and the relative value of the multiple reflection. FIG. 12 is a graph when the intermediate layer 9b of the ultrasound probe 10B has a predetermined configuration, showing the relations between the thickness of the reflection layer 5, the thickness of the intermediate layer 9a, and the relative value of the multiple reflection. FIG. 13 is a graph when the intermediate layer 9a of the ultrasound probe 10B has a predetermined configuration, showing the relations between the thickness of the reflection layer 5, the thickness of the intermediate layer 9b, and the relative value of the multiple reflection. FIG. 14 is a graph when the reflection layer 5 of the ultrasound probe 10B has a predetermined configuration, showing the relations between the thickness of the intermediate layer 9a, the thickness of the intermediate layer 9b, and the relative value of the multiple reflection. FIG. 15 is a graph when the reflection layer 5 of the ultrasound probe 10B has a predetermined configuration, showing the relations between the thickness of the intermediate layer 9a, the thickness of the intermediate layer 9b, and the relative value of the multiple reflection. FIG. 16 is a graph when the reflection layer 5 of the ultrasound probe 10B has a predetermined configuration, showing the relations between the thickness of the intermediate layer 9a, the thickness of the intermediate layer 9b, and the relative value of the multiple reflection.

Under the same conditions as the first embodiment, in the ultrasound probe 10B with the two intermediate layers 9a, 9B, the relative value of multiple reflection was calculated with different thicknesses of the reflection layer 5, different thicknesses of the intermediate layers 9a and 9b, and different acoustic impedances of the intermediate layer 9b. The acoustic impedance of the intermediate layer 9a was 3 MRayls, and the acoustic impedance of the intermediate layer 9b was 6 or 10 MRayls.

FIG. 11 shows the pattern of the relative value when the intermediate layer 9a is omitted, that is, when the intermediate layer 9b is a single layer with the acoustic impedance of 10 MRayls while the thickness of the reflection layer 5 and the thickness of the intermediate layer 9b are variable.

The vertical axis of the graph in FIG. 11 represents the relative value of multiple reflection of the ultrasound probe 10B. Unlike FIG. 5, it should be noted that the relative values of multiple reflection in FIG. 11 are ratios to an acceptable level of the multiple reflection, which is the value of the 0.5λ resonating configuration of a conventional piezoelectric element, as a reference of 0 dB. Thus, the satisfactory level of the relative value of multiple reflection is 0 dB or less. The horizontal axis represents the thickness of the intermediate layer 9b.

As is clearly shown in the results in FIG. 11, the relative value of multiple reflection is changed as the thickness of the intermediate layer 9b is changed. The relative value of multiple reflection is mostly 0 dB or less (the multiple reflection does not cause problems) when the thickness of the intermediate layer 9b is at least within the range of 0.06λ to 0.31λ. That is, multiple reflection can be reduced. The relative value of multiple reflection is mostly 0 dB or less when the thickness of the reflection layer 5 is within the range of 0.045λ to 0.075λ. That is, multiple reflection can be reduced. In the first embodiment, the relative value of multiple reflection is at a problematic level when the thickness of the reflection layer 5 is 0.05λ or more. However, in this embodiment, the intermediate layer 9b enables sufficient reduction of multiple reflection by adjusting the thickness of the intermediate layer 9b even when the reflection layer 5 is as thick as 0.1λ. While multiple reflection is 0 dB or more in some ranges, the multiple reflection can be reduced to 0 dB or less when the thickness of the intermediate layer 9b is approximately 0.16λ or more. The relative value of multiple reflection is lowered the most when the thickness of the reflection layer 5 is less than 0.05λ (0.045λ).

FIG. 12 shows calculation results of the relative values of multiple reflection of the ultrasound probe 10B with the two intermediate layers 9a and 9b, where: the thickness of the intermediate layer 9a is variable from 0 to 0.041λ; the thickness of the reflection layer 5 is variable from 0.045 to 0.01λ; the acoustic impedance of the intermediate layer 9a is 3 MRayls; and the acoustic impedance of the intermediate layer 9b is 10 MRayls. FIG. 12 shows the calculation results in the conditions where the acoustic impedance of the intermediate layer 9a was 3 MRayls, and the acoustic impedance of the intermediate layer 9b was 10 MRayls.

As is shown in the results in FIG. 12, the relative value of multiple reflection is at an acceptable level of 0 dB or less in all tested conditions. The relative value of multiple reflection is lowered the most when the thickness of the reflection layer 5 is less than 0.05λ (0.045λ).

The material of the intermediate layer 9a with an acoustic impedance of 3 MRayls may be an adhesive of a known epoxy resin, for example. The material of the intermediate layer 9b with an acoustic impedance of 10 MRayls may be an epoxy resin filled with tungsten or oxide particles, a composite material such as a graphite and metal powder, or carbides, for example.

The acoustic impedance of the intermediate layer 9a is 3 MRayls, and the acoustic impedance of the intermediate layer 9b is 10 MRayls, in the above-described examples. However, similar advantageous effects can be achieved in other configurations in which the acoustic impedance of the intermediate layer 9a is less than that of the intermediate layer 9b.

FIG. 13 shows calculation results of the relative values of the multiple reflection of the ultrasound probe 10B with the two intermediate layers 9a and 9b, where: the acoustic impedance of the intermediate layer 9a is 3 MRayls; the thickness of the intermediate layer 9a is 0.025λ; the thickness of the reflection layer 5 is variable from 0.045 to 0.1λ; the acoustic impedance of the intermediate layer 9b is 10 MRayls; and the thickness of the intermediate layer 9b is variable from 0.06 to 0.31λ.

FIG. 13 shows that the relative value of multiple reflection is at an acceptable level of 0 dB or less under any of these conditions. With the reflection layer 5 having a thickness of 0.1λ, the relative value is slightly above 0 dB when the thickness of the intermediate layer 9b is 0.06 or 0.31λ. However, the value is less than +0.3 dB, which is in an acceptable range, and the multiple reflection does not cause problems. The relative value of multiple reflection is lowered the most when the thickness of the reflection layer 5 is less than 0.05λ (0.045λ).

FIG. 14 shows calculation results of the relative values of multiple reflection of the ultrasound probe 10B with the two intermediate layers 9a and 9b, where: the thickness of the reflection layer 5 is fixed at 0.075λ; the thickness of the reflection layer 9a is 3 MRayls; the thickness of the intermediate layer 9a is variable from 0 to 0.124λ; the acoustic impedance of the intermediate layer 9b is 10 MRayls; and the thickness of the intermediate layer 9b is 0.06λ to 0.31λ.

FIG. 14 shows that the relative value of multiple reflection is at an acceptable level of 0 dB or less under any of these conditions. With the intermediate layer 9a having a thickness of 0.1λ or 0.124λ, the relative value is slightly above 0 dB when the thickness of the intermediate layer 9b is from 0.25 to 0.31λ. However, the value is less than +0.1 dB, which is still in an acceptable range in which the multiple reflection does not cause problems.

FIG. 15 shows calculation results of the relative values of the multiple reflection of the ultrasound probe 10B with the two intermediate layers 9a and 9b, where: the thickness of the reflection layer 5 is fixed at 0.075λ; the acoustic impedance of the intermediate layer 9a is 3 MRayls; the thickness of the intermediate layer 9a is variable from 0 to 0.124λ; the acoustic impedance of the intermediate layer 9b is 6 MRayls; and the thickness of the intermediate layer 9b is variable from 0.06 to 0.31λ. The relative value of multiple reflection is at an acceptable level of 0 dB or less under any of these conditions.

FIG. 16 shows calculation results of the relative values of the multiple reflection of the ultrasound probe 10B with the two intermediate layer 9a and 9b, where: the thickness of the reflection layer 5 is fixed at 0.075λ; the acoustic impedance of the intermediate layer 9a is 3 MRayls; the thickness of the intermediate layer 9a is variable from 0 to 0.124λ; the acoustic impedance of the intermediate layer 9b is 14 MRayls; and the thickness of the intermediate layer 9b is variable from 0.06 to 0.31λ. The relative value of multiple reflection is at an acceptable level of 0 dB or less under any of these conditions.

As described hereinbefore, it was revealed that multiple reflection can be reduced by selecting a suitable combination of the acoustic impedances in which the acoustic impedance of the intermediate layer 9a is less than that of the intermediate layer 9b as well as the thicknesses thereof even in a case where the reflection layer 5 is more than 0.05λ in thickness.

With this configuration, the ultrasound probe 10B can reduce multiple reflection so as not to affect the ultrasound image. Further, this configuration can facilitate improvement of the sensitivity of the ultrasound probe 10B and broadening the frequency more readily, and further improve the resolution of the ultrasound diagnostic apparatus 100.

As described hereinbefore, the ultrasound probe 10B includes the intermediate layer 9B in this embodiment. The intermediate layer 9B includes the intermediate layers 9a and 9b. The acoustic impedance of the intermediate layer 9a nearer to the reflection layer 5 is less than the acoustic impedance of the intermediate layer 9b nearer to the backing layer 4. Even when the thickness of the reflection layer 5 is out of the range of more than 0 to less than 0.05λ, this can reduce multiple reflection so as not to affect the ultrasound image, facilitates sensitivity improvement and wavelength broadening of the ultrasound probe 10B, and improve the resolution of the ultrasound diagnostic apparatus 100. Further, when the thickness of the reflection layer 5 is within the range of more than 0 to less than 0.05λ, this configuration can further reduce multiple reflection so as not to affect the ultrasound image, further facilitate the sensitivity improvement and wavelength broadening of the ultrasound probe 10B, and further improve the resolution of the ultrasound diagnostic apparatus 100.

The intermediate layers 9a and 9b in this embodiment are preferably electrically conductive so as to connect the signal electrode 3 to the signal electric terminal 7 of the piezoelectric element 1. However, in a case where the intermediate layers 9a and 9b are electrically insulative or semiconductive, the signal electrode 3, the reflection layer 5, and the signal electric terminal 7 of the piezoelectric element 1 may be electrically connected to each other by forming a conductor of copper or gold around the reflection layer 5 or in a through hole of the reflection layer 5 by plating, vapor deposition, or spattering.

In this embodiment, the reflection layer 5 and the intermediate layers 9a and 9b individually have a substantially uniform thickness. However, the intermediate layer 9B may have an uneven thickness that varies continuously, gradually, regularly, or irregularly. Further, the reflection layer 5 and/or the intermediate layers 9a, 9b may have an uneven pattern on one or both surfaces so as to have an uneven thickness as shown in FIGS. 9A to 9C. Similar advantageous effects can be achieved in these configurations. The average thickness is to be regarded as the thickness of the uneven intermediate layers 9a and 9b. In a case where the intermediate layer 9b is uneven in thickness on the surface facing the intermediate layer 9a as shown in FIGS. 9A to 9C, the gaps in the uneven patterns may be filled with the intermediate layer 9a. Since the intermediate layer 9b is in contact with the reflection layer 5, the intermediate layer 9b is electrically connected to and the reflection layer 5 when the intermediate layer 9b is conductive. Thus, the intermediate layer 9a may be made of an insulative material.

In this embodiment, the intermediate layer 9B is two-layered. Alternatively, the similar advantageous effects can be achieved in a case where the intermediate layer 9B includes three or more layers each of which has an acoustic impedance different from that of the adjacent layer.

In this embodiment, the multi-layered intermediate layer 9B is in contact with the reflection layer 5 as shown in FIG. 10. Alternatively, the similar advantageous effects can be achieved in a case where the multi-layered intermediate layer 9B is disposed between the signal electric terminal 7 and the backing 4 and/or between the reflection layer 5 and the signal electric terminal 7.

The above-described embodiments are preferred examples of the ultrasound probe and the ultrasound diagnostic apparatus according to the present invention, and the present invention is not limited to this. For example, two or more of the configurations of the above-described embodiments may be suitably combined.

Further, detailed configurations and detailed actions of the devices or the like of the ultrasound diagnostic apparatus 100 in the above embodiment and the like can also be appropriately modified without departing from the spirit of the present invention.

What is claimed is:

1. An ultrasound probe comprising:
a piezoelectric body that transmits and receives ultrasound for obtaining images of internal forms of a living subject;
a backing that is disposed behind the piezoelectric body; and
a reflector that is disposed between the piezoelectric body and the backing and that has an acoustic impedance greater than an acoustic impedance of the piezoelectric body; and
a plurality of intermediate layers disposed between the reflector and the backing, each intermediate layer of the plurality of intermediate layers having an acoustic impedance different from an acoustic impedance of the reflector and an acoustic impedance of the backing,
wherein an acoustic impedance of an intermediate layer of the plurality of intermediate layers nearer to the reflector is less than an acoustic impedance of an intermediate layer of the plurality of intermediate layers nearer to the backing,
wherein, a thickness of the piezoelectric body is approximately $0.25\lambda$ and a thickness of the reflector is within the range of more than 0 to less than $0.05\lambda$, where $\lambda$ is a wavelength of the ultrasound, and
wherein at least one intermediate layer of the plurality of intermediate layers has a substantially uniform thickness or has an uneven thickness that varies continuously, gradually, regularly, or irregularly.

2. The ultrasound probe according to claim 1, wherein the thickness of the reflector is within the range of $0.01\lambda$ to less than $0.05\lambda$, where $\lambda$ is the wavelength of the ultrasound.

3. The ultrasound probe according to claim 1, wherein the reflector has an uneven thickness that varies continuously, gradually, regularly, or irregularly.

4. The ultrasound probe according to claim 1, wherein the reflector has an uneven thickness and has an uneven pattern on a surface facing away from the piezoelectric body.

5. The ultrasound probe according to claim 1, wherein a plurality of materials of the plurality of intermediate layers are conductive.

6. An ultrasound probe comprising:
a piezoelectric body that transmits and receives ultrasound for obtaining images of internal forms of a living subject;
a backing that is disposed behind the piezoelectric body; and
a reflector that is disposed between the piezoelectric body and the backing and that has an acoustic impedance greater than an acoustic impedance of the piezoelectric body; and
an intermediate layer disposed between the reflector and the backing, the intermediate layer having an acoustic impedance different from an acoustic impedance of the reflector and an acoustic impedance of the backing,
wherein, a thickness of the piezoelectric body is $0.25\lambda$ and a thickness of the reflector is within the range of more than 0 to less than $0.05\lambda$, where $\lambda$ is a wavelength of the ultrasound, and
wherein the intermediate layer has an uneven thickness with an uneven pattern that varies irregularly such that ultrasound transmitted from the reflection layer to the intermediate layer is scattered by the uneven pattern.

7. The ultrasound probe according to claim 6, wherein the thickness of the reflector is within the range of $0.01\lambda$ to less than $0.05\lambda$, where $\lambda$ is the wavelength of the ultrasound.

8. The ultrasound probe according to claim 6, wherein the intermediate layer has an acoustic impedance that is greater than the acoustic impedance of the backing.

9. The ultrasound probe according to claim 6, wherein the thickness td of the reflection layer relative to the wavelength of the ultrasound, the acoustic impedance Zm of the intermediate layer, and a thickness tm of the intermediate layer relative to the wavelength of the ultrasound are in an area surrounded by a polyhedron with vertexes respectively at Points A1 to A18 in orthogonal coordinates (td, Zm, tm) of td, Zm, and tm:
Point A1 (0.01, 4, 0.02);
Point A2 (0.01, 4, 0.12);
Point A3 (0.01, 16, 0.02);
Point A4 (0.01, 16, 0.34);
Point A5 (0.01, 28, 0.02);
Point A6 (0.01, 28, 0.08);
Point A7 (0.03, 4, 0.02);
Point A8 (0.03, 4, 0.12);
Point A9 (0.03, 16, 0.02);
Point A10 (0.03, 16, 0.42);
Point A11 (0.03, 28, 0.4);
Point A12 (0.03, 28, 0.5);
Point A13 (0.049, 4, 0.02);
Point A14 (0.049, 4, 0.12);
Point A15 (0.049, 16, 0.18);
Point A16 (0.049, 16, 0.42);
Point A17 (0.049, 28, 0.42); and
Point A18 (0.049, 28, 0.5).

10. The ultrasound probe according to claim 6,
wherein the intermediate layer comprises a plurality of intermediate layers,
wherein an acoustic impedance of an intermediate layer nearer to the reflector is less than an acoustic impedance of an intermediate layer nearer to the backing.

11. The ultrasound probe according to claim 6, wherein a material of the intermediate layer is conductive.

12. The ultrasound probe according to claim 6, wherein the intermediate layer comprises an insulative or semiconductive material, and a conductor that is disposed around the insulative or semiconductive material or that penetrates the insulative or semiconductive material.

13. The ultrasound probe according to claim 6, wherein the intermediate layer has the uneven pattern on a surface facing away from the reflector.

14. An ultrasound diagnostic apparatus comprising:
the ultrasound probe according to claim 6;
a transmitter that generates a driving signal and outputs the driving signal to the ultrasound probe; and
an image generator that generates ultrasound image data based on a reception signal input from the ultrasound probe.

15. The ultrasound probe according to claim 6, wherein the intermediate layer has an acoustic impedance within a range including 4 to 28 MRayls.

16. The ultrasound probe according to claim 6, wherein the reflector has an even or uneven thickness.

17. The ultrasound probe according to claim 16, wherein the reflector has an uneven thickness that varies continuously, gradually, regularly, or irregularly.

18. The ultrasound probe according to claim 16, wherein the reflector has an uneven thickness and has an uneven pattern on a surface facing away from the piezoelectric body.

* * * * *